(12) United States Patent
Attia et al.

(10) Patent No.: US 12,387,847 B2
(45) Date of Patent: Aug. 12, 2025

(54) METHOD AND AN APPARATUS FOR DETECTING A LEVEL OF CARDIOVASCULAR DISEASE

(71) Applicant: Mayo Foundation for Medical Education and Research, Rochester, MN (US)

(72) Inventors: Itzhak Zachi Attia, Rochester, MN (US); Paul A. Friedman, Rochester, MN (US); Peter A. Noseworthy, Rochester, MN (US); Joerg Herrmann, Rochester, MN (US); Yash Gupta, Bangalore (IN); John Rincón-Hekking, Cambridge, MA (US); Ashim Prasad, Bangalore (IN); Rakesh Barve, Bengaluru (IN); Samir Awasthi, Boston, MA (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 18/648,292

(22) Filed: Apr. 26, 2024

(65) Prior Publication Data
US 2024/0363247 A1  Oct. 31, 2024

Related U.S. Application Data

(60) Provisional application No. 63/499,004, filed on Apr. 28, 2023.

(51) Int. Cl.
*G16H 50/20* (2018.01)
*A61B 5/00* (2006.01)
(Continued)

(52) U.S. Cl.
CPC ............. *G16H 50/20* (2018.01); *A61B 5/341* (2021.01); *A61B 5/346* (2021.01); *A61B 5/7267* (2013.01); *G16H 10/60* (2018.01)

(58) Field of Classification Search
None
See application file for complete search history.

(56) References Cited

U.S. PATENT DOCUMENTS 11,756,688 B2  9/2023  Ulloa-Cerna et al.
2019/0286242 A1*  9/2019  Ionescu ................. G06N 3/084
(Continued)

FOREIGN PATENT DOCUMENTS

CN  116196013 A  6/2023
IN  202341049815 A  9/2023
(Continued)

OTHER PUBLICATIONS

Gliner, V., Keidar, N., Makarov, V. et al. Automatic classification of healthy and disease conditions from images or digital standard 12-lead electrocardiograms. Sci Rep 10, 16331 (2020). https://doi.org/10.1038/s41598-020-73060-w (Year: 2020).*

(Continued)

*Primary Examiner* — Robert A Sorey
(74) *Attorney, Agent, or Firm* — Caldwell Intellectual Property Law

(57) ABSTRACT

An apparatus and method for detecting a level of cardiovascular disease. The apparatus includes at least a processor and a memory communicatively connected to the at least a processor, wherein the memory contains instructions configuring the at least a processor to: receive a plurality of voltage-time data, generate at least a feature vector from the voltage-time data by at least a feature model, input the at least feature vector into a cardiovascular classification model, generate at least a disease indication in a subject using the classification model, wherein the disease indication comprises a level of myocarditis, and display the at least a disease indication.

20 Claims, 17 Drawing Sheets

(51) Int. Cl.
*A61B 5/341* (2021.01)
*A61B 5/346* (2021.01)
*G16H 10/60* (2018.01)

(56) References Cited

U.S. PATENT DOCUMENTS

2022/0384044 A1* 12/2022 Ulloa-Cerna .......... G16H 50/70
2023/0143594 A1*  5/2023 Yu ......................... G16H 50/20
                                                              600/523
2025/0064374 A1*  2/2025 Luo ........................ A61B 5/361

FOREIGN PATENT DOCUMENTS

| WO | 2023212297 | A1 | 11/2023 |
| WO | 2023224948 | A1 | 11/2023 |

OTHER PUBLICATIONS

M. Jafari et al; Automatic Diagnosis of Myocarditis Disease in Cardiac MRI Modality using Deep Transformers and Explainable Artificial Intelligence; In book: Artificial Intelligence in Neuroscience: Affective Analysis and Health Applications (pp. 145-155) Oct. 2022.

* cited by examiner

METHOD AND AN APPARATUS FOR DETECTING A LEVEL OF CARDIOVASCULAR DISEASE

CROSS-REFERENCE TO RELATED APPLICATIONS

This application claims the benefit of priority of U.S. Provisional Patent Application Ser. No. 63/499,004, filed on Apr. 28, 2023, and titled "DEEP LEARNING MODEL FOR SCREENING PATIENTS FOR MYROCARDITIS USING OUTPUT OF A 12-LEAD ELECTROCARDIOGRAM," which is incorporated by reference herein in its entirety.

FIELD OF THE INVENTION

The present invention generally relates to the field of medical scanning apparatuses. In particular, the present invention is directed to a method and an apparatus for detecting a level of cardiovascular disease.

BACKGROUND

Classification of medical scan data can be hampered by an overabundance of potential parameters. This can make it difficult for a model trained in classification to converge to a sufficient degree, undermining the value of such models in diagnostics or detection.

SUMMARY OF THE DISCLOSURE

In an aspect, an apparatus for detecting cardiovascular disease. An apparatus includes at least a processor and a memory communicatively connected to the at least a processor, wherein the memory contains instructions configuring the at least a processor to: receive a plurality of voltage-time data, generate at least a feature vector from the voltage-time data by at least a feature model, input the at least feature vector into a cardiovascular classification model, generate at least a disease indication in a subject using the classification model, wherein the disease indication comprises a level of myocarditis, and display the at least a disease indication.

In another aspect a method for detecting cardiovascular disease. The method includes using at least a processor configured to receive a plurality of voltage-time data, generate at least a feature vector from the voltage-time data by at least a feature model, input the at least feature vector into a cardiovascular classification model, generate at least a disease indication in a subject using the classification model, wherein the disease indication comprises a level of myocarditis, and display the at least a disease indication.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for detecting a level of cardiovascular disease.

Aspects of the present disclosure can be used to detect levels of myocarditis without invasive testing. Myocarditis is an acquired cardiomyopathy that results from inflammation of cardiac muscle and can be caused from a variety of etiologies including cancer, immunotherapy, auto-immune diseases, vaccinations and infections such as COVID-19. Aspects of the present disclosure can be used in the detection of cardiovascular diseases and conditions. This is so, at least in part, because the invention disclosed used in conjunction with standard-of-care protocols may be used to hone different diagnosis and risk stratify patients (e.g., performed prior to, following, or concomitantly with a troponin lab test).

Aspects of the present disclosure allow for integration with artificial intelligence namely neural networks to detect cardiovascular diseases or conditions using paired 12 and 6 lead ECG. Exemplary embodiments illustrating aspects of the present disclosure are described below in the context of several specific examples.

In some embodiments, feature detection stages enable downstream models and/or classifiers to converge more effectively with less data. This may improve computational and storage resource consumption; the ability of a computing device or apparatus so configured to make accurate detection and/or classification may also be enhanced.

Figure 1:
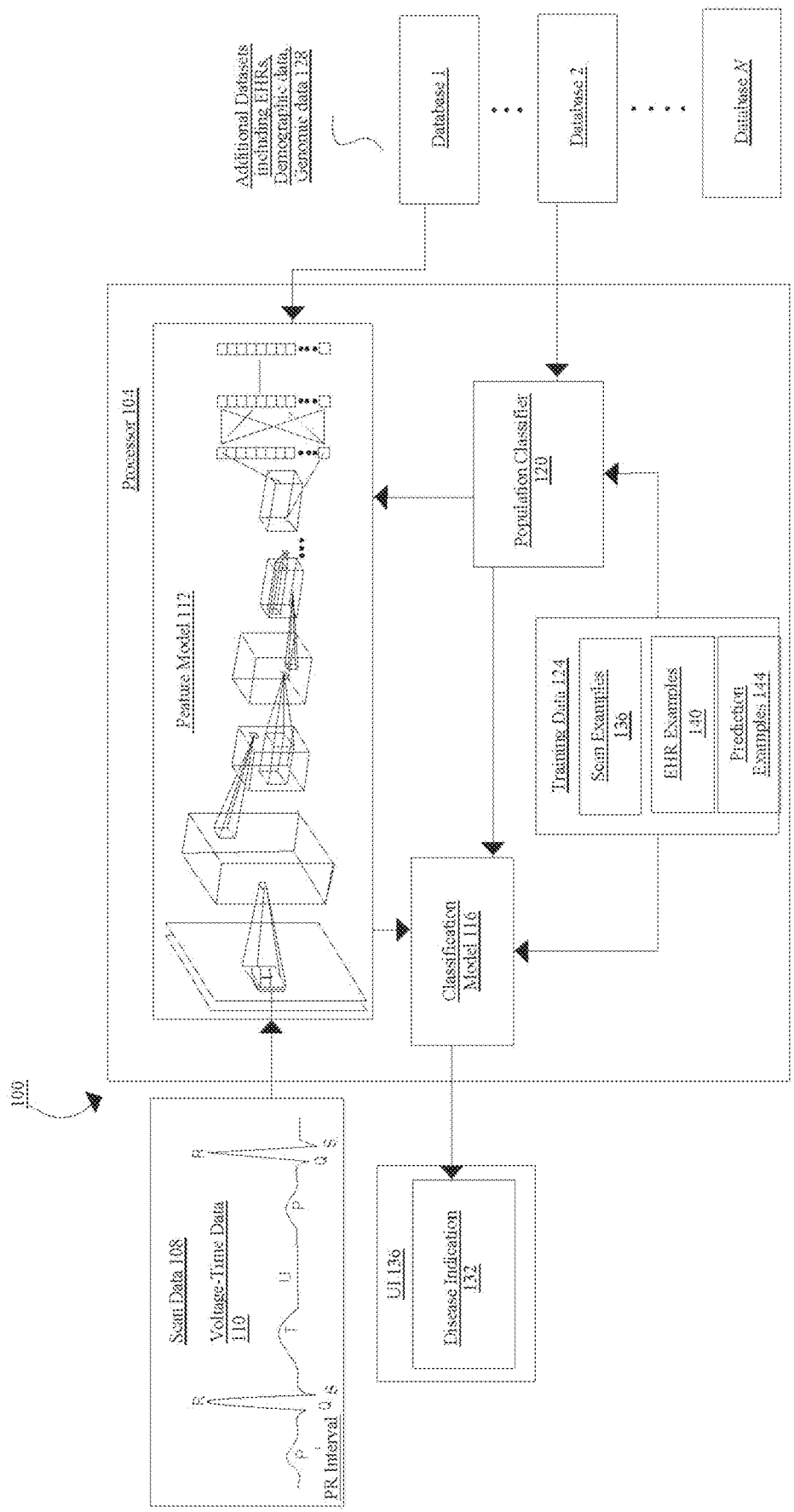
FIG. 1 is a block diagram of an exemplary embodiment of an apparatus for detecting a level of cardiovascular disease.

Referring now to FIG. 1, an exemplary embodiment of an apparatus 100 for detecting a level of cardiovascular disease is illustrated. Apparatus 100 includes a processor. Apparatus 100 includes a processor communicatively connected to a memory. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1, processor 104 may include any computing device as described in this disclosure, including without limitation a microcontroller, microprocessor, digital signal processor (DSP) and/or system on a chip (SoC) as described in this disclosure. Processor 104 may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented, as a non-limiting example, using a "shared nothing" architecture.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, processor 104 may be configured to receive a plurality of scan data 108. For the purposes of this disclosure, "scan data" 108 is a set of digital and/or analog recordings and/or measurements obtained by capturing physiological signals and/or imaging data related physiological states and/or processes of a human or animal body. Capture of signals may involve non-invasive techniques to gather information about specific aspects of an individual's health such as cardiac activity, brain function, or anatomical structures; invasive processes and/or processes involving catheterization and/or introduction of dyes, contrasts, emitters of electromagnetic radiation, positron emitters or the like into tissue may also be included in non-limiting examples. Scan data 108 may include voltage-time data 110. "Voltage-time data," for the purposes of this disclosure, is data that depends on voltage and time. Examples of these may be the electrical signaling in Electrocardiograms (ECG), Electroencephalogram (EEG), and/or Echocardiogram (Echo) representing voltage-time data, and/or imaging data. For example, an ECG may include voltage-time data 110. Scan data may include time-series recordings, images or other digital representations obtained through specialized equipment and sensors; for instance, scan data may be provided in voltage versus time form. ECG may include the waveform from the electrocardiograph derived from twelve or six lead wires setup. It should be noted that the values from the electrocardiograph may include specific ECG components such as P wave, QRS complex, T wave, U wave, PR Interval, QT interval, ST segment etc. These components may be voltages and time measurements. Scan data may also include Echocardiogram data. Scan data may also include EEG which measure the electrical activity from small metal electrodes attached to the scalp of a subject. It should be noted that the values of EEGs may include signals that represent the collective activity of millions of neurons firing synchronously in the brain. Components of EEG signals may include: background activity or alpha waves; beta waves, event-related potentials or P300, N100, P200, N200; Sleep Spindles and K-Complexes, seizure activity detailing epileptiform and sharp waves, etc. Processor 104 may be further configured to receive electronic health records (EHR), additional datastores, demographic information, genomic information and any cardiovascular related data relating to patient diagnosis. The receipt of the electronic health records, additional datastores, and demographic information may include communicating with a database or databases responsible for hosting subject medical record information. It should be noted that additional datastores 128 may include de-identified patient. This medical record information may be received over a communications protocol. For the purposes of this disclosure, "communications protocol" is a set of rules describing how to transmit, exchange or receive data across a network. It should be noted that the protocol used in communicating with a database may be standardized or unstandardized and be text-based, binary, or some other base.

Still referring to FIG. 1, in some embodiments, processor 104 may further be configured to receive to a feature vector when input to a classification model 116. In some embodiments, processor 104 may also receive genomic data which also received to the feature vector when input to a classification model 116. Without being bound by any particular methodology or theory said genomic data may be derived from a biological sample that is derived from a patient predisposed to increased cardiovascular risk, e.g. family history or genetic and/or protein markers.

Still referring to FIG. 1, processor 104 may be further configured to train a feature model 112 using a plurality of electronic health records (EHR). For purposes of this disclosure, "feature model" 112 is a type of machine learning model which identifies and optimizes cardiovascular patterns, structures, or characteristics, otherwise known as 'features' from raw data to enhance performance of feature vector creation. Feature model 112 may be implemented in any suitable manner, including without limitation using a k-means clustering model, a particle swarm optimization model, and/or a neural network such as without limitation a convolutional neural network. Training feature model 112 may include preprocessing a plurality of electronic health records (EHR). Preprocessing may include collecting a plurality of EHRs and/or data thereof from sources such as EHR systems, wearable devices, or medical databases; data may include information such as without limitation demographics, medical history, diagnostic tests, vital signs, and treatment records. Preprocessing may include cleaning data within and/or from EHRs. Data cleaning may include image enhancement and/or improvement and error correction using error correction codes (ECC). Image enhancement and/or improvement may include noise reduction techniques such as filtering (e.g. median filtering, Gaussian filtering), denoising algorithms (e.g., wavelet denoising, bilateral filtering), or image restoration methods (e.g. deconvolution), and may be applied to remove or reduce noise from images, enhancing their visual quality and making them more suitable for analysis. Images may exhibit poor contrast or brightness levels, leading to loss of detail and information. Data cleaning methods, such as histogram equalization, contrast stretching, or gamma correction may be employed to adjust the contract and brightness levels, of images, enhancing their visual appearance and improving visibility of important features or structures. Image enhancing may further include artifact removal. Image artifacts, such as scratches, dust, or compression artifacts, may distort image content and introduce unwanted features. Data cleaning techniques, such as inpainting, morphological operations, or content-aware filling may be used to remove or repair artifacts from images, restoring their original appearance and improving their suitability for analysis and interpretation. The types of techniques may be used on imaging received from scan data 108.

Further referring to FIG. 1, error correction using error correction code (ECC) may including data preprocessing steps to identify and correct errors or inconsistencies in the input data from scan data 108 or data from additional datasets 128. An error correction code, also known as error correcting code (ECC), is an encoding of a message or lot of data using redundant information, permitting recovery of corrupted data. In an example, in digital image transmission systems, preprocessing may involve error detection techniques (e.g. checksums, cyclic redundancy checks) to identify corrupted or missing data packets and discard or replace them before error correction. Error correction codes, such as Reed-Solomon codes, convolutional codes, or Hamming codes, may be employed to detect and correct errors in digital data transmission or storage systems. These codes add redundancy to the transmitted data, allowing the receiver to detect and correct errors caused by noise, interference or transmission errors. After error correction, post processing steps may be performed to further refine the corrected data and ensure its integrity. This may involve validation checks, data integrity verification, or additional error detection and correction techniques to address residual errors or inconsistencies.

Continuing to refer to FIG. 1, preprocessing may include extracting relevant EHR features. The relevance of features extracted from EHRs or scan data 108 may be determined by their ability to capture meaningful information related to the task at hand for example: disease prediction, risk assessment, or treatment outcome prediction. Features may be considered relevant if they provide insights into the underlying physiological processes, clinical characteristics, or predictive factors associated with the target outcome. Extraction may involve domain specific knowledge and techniques such as transforming categorical variables into numerical representations, encoding temporal information, or aggregating data over time windows. Extracting feature vectors from scan data 108 and medical records (i.e. additional datasets 128) may involve aligning the extracted features with vectors representing cardiovascular diseases. During extraction of feature vectors from scan data 108 and medical records 128, the objective may be to map the extracted features to vectors that represent various cardiovascular diseases or conditions. This mapping process may involve associating the features derived from cardiovascular measurements, such as ECG signals, EEG signals or imaging, Echo signals or imaging, blood pressure readings, with specific disease states or diagnostic categories. Furthermore, features obtained from medical records 128, including demographic data 128, medical history and laboratory test results, are linked to corresponding disease vectors. By aligning the extracted feature vectors with disease vectors, feature model 112 may learn to identify patterns and/or signatures in the feature space that are indicative of various cardiovascular diseases based on the combined information from scan data 108 and medical records or additional datasets 128, enabling accurate diagnosis, risk assessment, and treatment planning in clinical practice.

Still referring to FIG. 1, in an embodiment, feature model 112 may include detecting patterns consistent with errors using a trained neural network which may involve preparing annotated training data comprises error-free and erroneous instances, using a neural network for binary classification, training a neural network to identify error patterns through supervised learning, and evaluating its performance on a validation data set. A neural network may learn to distinguish between error-free and erroneous data instances by optimizing parameters through backpropagation and gradient descent. Once validated, the neural network may continue receiving and processing incoming data such as scan data 108 and additional datasets 128 which may include flagging instances exhibiting error patterns for intervention or correction.

With continued reference to FIG. 1, cleaning data may include filling in missing information when received from scan data 108 and/or additional datasets 128. In one or more embodiments, processor 104 may implement one or more aspects of "generative artificial intelligence (AI)," a type of AI that uses machine learning algorithms to create, establish, or otherwise generate data such as, without limitation, scan data 108 and/or data from additional datasets 128 and/or the like in any data structure as described herein (e.g., text, image, video, audio, among others) that is similar to one or more provided training examples. In an embodiment, machine learning module described herein may generate one or more generative machine learning models that are trained on one or more set of EHR examples 140, Scan examples 136, prediction examples 144. One or more generative machine learning models may be configured to generate new examples that are similar to the training data of the one or more generative machine learning models but are not exact replicas; for instance, and without limitation, data quality or attributes of the generated examples may bear a resemblance to the training data provided to one or more generative machine learning models, wherein the resemblance may pertain to underlying patterns, features, or structures found within the provided training data.

Still referring to FIG. 1, in some cases, generative machine learning models may include one or more generative models. As described herein, "generative models" refers to statistical models of the joint probability distribution P(X, Y) on a given observable variable x, representing features or data that can be directly measured or observed (e.g., scan data such as ECG signals, EEG signals or imaging, Echo imaging etc.) and target variable y, representing the outcomes or labels that one or more generative models aims to predict or generate (e.g., information contained in integrated feature vectors for classification in disease indication 132). In some cases, generative models may rely on Bayes theorem to find joint probability; for instance, and without limitation, Naïve Bayes classifiers may be employed by computing device to categorize input data such as, without limitation, scan data such as ECG signals, EEG signals or imaging, Echo imaging etc. into different classes or categories etc. such as, without limitation, disease indication and risk assessment and others etc.

In a non-limiting example, and still referring to FIG. 1, one or more generative machine learning models may include one or more Naïve Bayes classifiers generated, by computing device, using a Naïve bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)+P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing Device may then calculate a likelihood table by calculating probabilities of different data entries and classification labels. Processor 104 may utilize a naïve Bayes equation to calculate a posterior probability for each class. A class containing the highest posterior probability is the outcome of prediction.

Still referring to FIG. 1, although Naïve Bayes classifier may be primarily known as a probabilistic classification algorithm; however, it may also be considered a generative model described herein due to its capability of modeling the joint probability distribution P(X, Y) over observable variables X and target variable Y. In an embodiment, Naïve Bayes classifier may be configured to make an assumption that the features X are conditionally independent given class label Y, allowing generative model to estimate the joint distribution as P(X, Y)=P(Y)ΠiP(Xi|Y), wherein P(Y) may be the prior probability of the class, and P($X_i$|Y) is the conditional probability of each feature given the class. One or more generative machine learning models containing Naïve Bayes classifiers may be trained on labeled training data, estimating conditional probabilities $P(X_i|Y)$ and prior probabilities $P(Y)$ for each class; for instance, and without limitation, using techniques such as Maximum Likelihood Estimation (MLE). One or more generative machine learning models containing Naïve Bayes classifiers may select a class label y according to prior distribution $P(Y)$, and for each feature $X_i$, sample at least a value according to conditional distribution $P(X_i|y)$. Sampled feature values may then be combined to form one or more new data instance with selected class label y. In a non-limiting example, one or more generative machine learning models may include one or more Naïve Bayes classifiers to generate new examples of scan data 108 based on high risk or disease indication etc. (e.g high risk or disease indication in a specific demographic class), wherein the models may be trained using training data containing a plurality of features e.g., data features if any or simply "features of scan data examples", and/or the like as input correlated to a plurality of labeled classes e.g., high risk for an assortment of patients in a demographic class as output.

Still referring to FIG. 1, in some cases, one or more generative machine learning models may include generative adversarial network (GAN). As used in this disclosure, a "generative adversarial network" is a type of artificial neural network with at least two sub models (e.g., neural networks), a generator, and a discriminator, that compete against each other in a process that ultimately results in the generator learning to generate new data samples, wherein the "generator" is a component of the GAN that learns to create hypothetical data by incorporating feedbacks from the "discriminator" configured to distinguish real data from the hypothetical data. In some cases, generator may learn to make discriminator classify its output as real. In an embodiment, discriminator may include a supervised machine learning model while generator may include an unsupervised machine learning model as described in further detail with reference to FIG. 2.

With continued reference to FIG. 1, in an embodiment, discriminator may include one or more discriminative models, i.e., models of conditional probability $P(Y|X=x)$ of target variable Y, given observed variable X. In an embodiment, discriminative models may learn boundaries between classes or labels in given training data. In a non-limiting example, discriminator may include one or more classifiers as described in further detail below with reference to FIG. 2 to distinguish between different categories e.g., correct vs. incorrect, or states e.g., TRUE vs. FALSE within the context of generated data such as, without limitations, disease indication 132 and/or the like. In some cases, computing device may implement one or more classification algorithms such as, without limitation, Support Vector Machines (SVM), Logistic Regression, Decision Trees, and/or the like to define decision boundaries.

In a non-limiting example, and still referring to FIG. 1, generator of GAN may be responsible for creating synthetic data that resembles real scan data examples 140 as consideration for disease indication 132. In some cases, GAN may be configured to receive scan data 108 and/or additional datasets 128 such as, without limitation, ECG signals, EEG signals or imaging etc., as input and generates corresponding scan data examples 140 as consideration for disease indication 132 containing information describing or evaluating the performance of one or more voltage timing data from ECG or image clarity from EEG or Echocardiogram. On the other hand, discriminator of GAN may evaluate the authenticity of the generated content by comparing it to real scan data examples 140 as consideration for disease indication 132, for example, discriminator may distinguish between genuine and generated content and providing feedback to generator to improve the model performance.

With continued reference to FIG. 1, in other embodiments, one or more generative models may also include a variational autoencoder (VAE). As used in this disclosure, a "variational autoencoder" is an autoencoder (i.e., an artificial neural network architecture) whose encoding distribution is regularized during the model training process in order to ensure that its latent space includes desired properties allowing new data sample generation. In an embodiment, VAE may include a prior and noise distribution respectively, trained using expectation-maximization meta-algorithms such as, without limitation, probabilistic PCA, sparse coding, among others. In a non-limiting example, VEA may use a neural network as an amortized approach to jointly optimize across input data and output a plurality of parameters for corresponding variational distribution as it maps from a known input space to a low-dimensional latent space. Additionally, or alternatively, VAE may include a second neural network, for example, and without limitation, a decoder, wherein the "decoder" is configured to map from the latent space to the input space.

In a non-limiting example, and still referring to FIG. 1, VAE may be used by computing device to model complex relationships between scan data 108 and/or additional datasets 128 e.g., ECG data. In some cases, VAE may encode input data into a latent space, capturing scan data 108 for consideration in disease indication 132. Such encoding process may include learning one or more probabilistic mappings from observed scan data 108 and/or additional datasets 128 to a lower-dimensional latent representation. Latent representation may then be decoded back into the original data space, therefore reconstructing the scan data 108 and/or additional datasets 128. In some cases, such decoding process may allow VAE to generate new examples or variations that are consistent with the learned distributions.

With continued reference to FIG. 1, in some embodiments, one or more generative machine learning models may be trained on a plurality of Echo image data or sound data as described herein, wherein the plurality of Echo image data may provide visual/acoustical information that generative machine learning models analyze to understand the dynamics of Doppler ultrasound in an Echocardiogram. In some cases, such data may help generative machine learning models to learn appropriate language and tone for providing frequency output from Doppler response. Additionally, or alternatively, one or more generative machine learning models may utilize one or more predefined templates representing, for example, and without limitation, correct scan data examples 140 as consideration for disease indication 132.

Still referring to FIG. 1, processor 104 may configure generative machine learning models to analyze input data such as, without limitation, scan data 108 to one or more predefined templates such as scan data template from training data representing correct scan data examples 140 as consideration for disease indication 132 described above, thereby allowing computing device to identify discrepancies or deviations from correct disease indication. In some cases, processor 104 may be configured to pinpoint specific errors in scan data 108 or any other aspects of the additional datasets 128. In a non-limiting example, computing device may be configured to implement generative machine learning models to incorporate additional models to detect sound or Doppler response from Echo data as another example. In some cases, errors may be classified into different categories or severity levels. In a non-limiting example, some errors may be considered minor, and generative machine learning model such as, without limitation, GAN may be configured to generate scan data examples 140 as consideration for disease indication 132 contain only slight adjustments while others may be more significant and demand more substantial corrections. In some embodiments, processor 104 may be configured to flag or highlight image errors, altering the scan data 108 to areas that need correction, directly on the scan data 108 and/or additional datasets 128 using one or more generative machine learning models described herein. In some cases, one or more generative machine learning models may be configured to generate and output indicators such as, without limitation, visual indicator, audio indicator, and/or any other indicators as described above. Such indicators may be used to signal the detected error described herein.

Still referring to FIG. 1, in some cases, processor 104 may be configured to identify and rank detected common deficiencies (e.g. degraded image or loss of signal) across plurality of scan data 108; for instance, and without limitation, one or more machine learning models may classify errors in a specific order e.g., lack of clarity in image data from Echocardiogram in a descending order of commonality. Such ranking process may enable a prioritization of most prevalent issues, allowing instructors or processor 104 to address the lack of clarity in the image from an Echocardiogram. In a non-limiting example, to rectify an error in an echocardiogram image data augmentation to diversify the data set and reduce the influence of artifacts, improve preprocessing techniques such as denoising filters, contrast enhancement or fine-tuning model architecture and hyperparameters through method like grid or random search.

Still referring to FIG. 1, in some cases, one or more generative machine learning models may also be applied by computing device to edit, modify, or otherwise manipulate existing data or data structures. In an embodiment, output of training data used to train one or more generative machine learning models such as GAN as described herein may include scan data examples 136, EHR examples 140 that linguistically or visually demonstrate modified scan data 108 and/or additional datasets 128 e.g., discretizing of ECG signals etc., and/or the like. In some cases, scan data examples 140 as consideration for disease indication 132 may be synchronized with scan data 108 and/or additional datasets 128, for example, and without limitation, in a side-by-side or even overlayed arrangement with the input user action data, providing real-time visual guidance. In some cases, such scan data examples 140 as consideration for disease indication 132 may be integrated with the scan data 108 and/or additional datasets 128, offering user a multisensory instructional experience.

Additionally, or alternatively, and still referring to FIG. 1, computing device may be configured to continuously monitor scan data 108 and/or additional datasets 128. In an embodiment, computing device may configure discriminator to provide ongoing feedback and further corrections as needed to subsequent input data (e.g., image, electrical signaling). In some cases, one or more sensors such as, without limitation, wearable device, motion sensor, or other sensors or devices described herein may provide additional datasets 128 that may be used as subsequent input data or training data for one or more generative machine learning models described herein. An iterative feedback loop may be created as computing device continuously receive real-time data, identify errors as a function of real-time data, delivering corrections based on the identified errors, and monitoring user response and/or device response signal on the delivered corrections. In an embodiment, processor 104 may be configured to retrain one or more generative machine learning models based on scan data examples 140 or update training data of one or more generative machine learning models by integrating scan data example 140 into the original training data. In such embodiment, iterative feedback loop may allow machine learning module to adapt to the filling in missing information, enabling one or more generative machine learning models described herein to learn and update based on scan data examples 140 and generated feedback.

With continued reference to FIG. 1, other exemplary embodiments of generative machine learning models may include, without limitation, long short-term memory networks (LSTMs), (generative pre-trained) transformer (GPT) models, mixture density networks (MDN), and/or the like. As an ordinary person skilled in the art, upon reviewing the entirety of this disclosure, will be aware of various generative machine learning models may be used generating a feature vector and inputting into classification model 116.

Still referring to FIG. 1, preprocessing may include normalizing said EHR features and/or feature vectors; normalization may be performed in any manner described below, and may normalize numerical features and/or feature vectors, e.g., to ensure that they have similar scales, which may improve the convergence and stability of the training process. Preprocessing may include splitting data into a plurality of data sets for training, validation and test. In a non-limiting example, a training set may be used to train the model, a validation set may be used to tune hyperparameters and monitor the model's performance during training, and a test set may be used to evaluate the model's generalized performance on unseen data. Second, training may then include configuring layers and/or activation functions of a feature model 112. This incudes defining examples of different sorts of structures a neural network may have. Training may include executing the plurality of data sets in a feature model 112 while tuning a plurality of hyperparameters. For the purposes of this disclosure, "hyperparameters" are parameters that are set prior to the training process and control the behavior of a machine learning model. Examples of hyperparameters may include learning rate, batch size, regularization strength, number of layers, number of neurons per layer, activation functions, optimizer, loss functions, metrics etc. Hyperparameters may be external configuration settings that influence the learning process itself.

Still referring to FIG. 1, an embodiment of loss function selection may include a loss function that reflects the objective of the task, such as binary-cross entropy for binary classification tasks, such as disease predictions, or means squared error for regression tasks, such as predicting patient outcomes. For the purposes of this disclosure, "loss function" is an expression of an output of which an optimization algorithm minimizes to generate an optimal result. Loss function may define the objective function used to measure the difference between the model's predictions and the true labels during training, guiding the optimization process towards better performance. One type of loss function may be mean squared error (MSE). A MSE may be used for regression tasks, where the goal is to minimize the squared differences between predicted and actual continuous values. Tuning a MSE loss function may not have hyperparameters to tune directly. However, tuning the learning rate or regularization strength may indirectly affect the optimization process and the convergence behavior of the model when using MSE. Processor 104, containing machine learning models may be trained using MSE loss to predict a patient's risk in developing cardiovascular disease based on their demographic information, medical history and clinical biomarkers, scan data 108 and may be included in disease indication 132.

Another embodiment of a loss function may be binary cross-entropy (BCE). BCE may be used for binary classification tasks, where the target variable has two possible outcomes (e.g., 0 or 1). BCE measures the difference between predicted probabilities and true binary labels. Tuning a BCE loss function may not include hyperparameters to tune directly. However, the learning rate and regularization strength may impact the optimization process and model performance when using BCE. A BCE model trained using BCE loss may predict whether a patient is at high risk of developing a specific cardiovascular disease condition based on their medical history, lifestyle factors, and diagnostic test results from scan data 108. This may be included in disease indication 132.

Another embodiment of a loss function may include Huber loss. Huber loss may be used for regression tasks that are sensitive to outliers. It combines the best properties of MSE and absolute error loss by penalizing large errors linearly and small errors quadratically. Tuning a Huber loss may include using a hyperparameter called a delta parameter, which determines the threshold for distinguishing between quadratic and linear regions of the loss function. Tuning the delta parameter may adjust the balance between robustness to outliers and sensitivity to small errors. As a nonlimiting example, a regression model trained using Huber loss may predict continuous outcomes for cardiovascular disease including estimating the progression of a patient's arterial stiffness or the change in left ventricular ejection fraction over time from scan data 108. Results of Huber loss may be included in disease indication 132. Methods and systems for generating a disease indication may be consistent with the disclosure of U.S. patent application Ser. No. 17/552,246, filed on Dec. 15, 2021, and entitled, "SYSTEMS AND METHODS FOR DIAGNOSING A HEALTH CONDITION BASED ON PATIENT TIME SERIES DATA," the entirety of which is incorporated herein by reference.

Still referring to FIG. 1, processor 104 may further be configured to train a feature model 112 using training data classified and/or sorted using a population classifier 120 machine learning model. As discussed below, a population classifier may be designed to categorize individuals into different groups or classes based on various attributes, typically derived from medical records (i.e., EHRs), demographic data, genomic data, and other relevant information. A population classifier may be trained with a plurality of EHRs and prediction data correlated to a plurality of EHR examples 140 and prediction data examples 144. A population classifier 120 may input the plurality of EHR and prediction data examples 144 into the machine learning model. A population classifier 120 outputs a prediction of the level of cardiovascular disease in a population set. It should be noted that training data 124 here may be externally or locally supplied. It should further be noted that training data 124 correlates to diverse sets of the population with different diagnostic data relating to cardiac health. A population classifier 120 may be configured to receive training data 124 that emulates EHRs, test set ECGs, EEGs, Echocardiograms, demographic data enough to classify a population set to cardiac health and cardiovascular deficiencies. Examples in training data 124 may contain EHRs, ECGs, demographic data, genomic information, confirmation data on cardiovascular deficiencies and diseases. In a population classifier 120, individuals are being classified into different groups or categories based on various attributes which may be derived from their medical records or other relevant information. Population classifier 120 may aim to identify patterns or relationships within the example data training it that distinguishes between different subgroups. In a nonlimiting example, this would include individuals with a particular medical condition, those at risk of developing certain diseases, or those with similar demographic lifestyle characteristics. This classification is fed into a classification model 116 for consideration of a disease indication discussed below. Population classifier may contain a performance enhancement program. A performance enhancement program may act as a rational agent to predict the most accurate diagnosis of cardiovascular disease within a given population set. The result may be in machine-readable format and/or other formats. In non-limiting examples, these formats may include CSV (comma-separated values), JSON (JavaScript Object Notation), HDF5 (Hierarchical Data Format version 5), DICOM (Digital Imaging and Communications in Medicine), XML (Extensible Markup Language), RDF (Resource Description Framework), etc.

Still referring to FIG. 1, feature model 112 generates a feature vector and adds it to the feature vector from the plurality of scan data. Generation of a feature vector may include representing the extracted features from scan data 108. Generation may further include feature extraction from cardiovascular measurements or scan data 108. Feature extraction may include extracting from medical records (i.e. EHRs, demographic data, additional datasets 128), integration of these feature vectors and training and/or fine tuning. Feature model 112 may receive scan data, which may include ECG signals, EEG signals, Echo signals, electromyograms (EMGs), Electrooculogram (EOGs) or any other type of scan data as described above, and groups such data to features. Features may be generated and/or identified by feature model by identifying centroids about which scan data may group; alternatively or additionally features may be labeled and/or previously identified, for instance via user inputs. In a nonlimiting example, scan data may be passed through convolutional layers that learn to extract patterns indicative of specific physiological signals which may pertain to physical abnormalities. In a vector for feature learning from scan data, each value represents a specific feature extracted from the type of scan data relevant to physiological signals. These features capture the various characteristics or patterns present in physiological signals, such as data within ECGs, EEGs, electromyograms (EMGs), Electrooculogram (EOGs) and others. The relationship between the vector values and the features of physiological signals may be in how each value quantifies a particular aspect of the physiological signal, providing numerical representations of the physical phenomena relevant to cardiac activity, brain activity, skeletal activity, eye measurement activity and others. For example, a value in the vector may represent duration of an EEG signal in a specific part of the brain, while another value might represent a durational skeletal electrical signal in another part of the body and so one depending on the type of measurement tests a patient has completed. By analyzing these features collectively, healthcare professionals may gain insights into a patient's overall electrical activity and health, identify abnormalities, and make diagnostic or prognostic assessments.

In another nonlimiting more specific example, an ECG signal may be passed through convolutional layers that learn to extract patterns indicative of various cardiac abnormalities, such as arrhythmias, ischemia, or conduction disorders. It should be noted, for an ECG nonlimiting example, that in a vector using for feature learning from ECG data, each value represents a specific feature extracted from the ECG signal. These features capture various characteristics or patterns present in the ECG waveform, such as amplitude, duration, frequency, or morphology of different ECG components (e.g. P wave, QRS complex, T wave). The relationship between the vector values and the features may be in how each value quantifies a particular aspect of the ECG signal, providing numerical representations of physiological phenomena relevant to cardiac activity. For example, a value in the vector may represent a duration of the QRS complex, while another value might represent the amplitude of the T wave. By analyzing these feature values collectively, healthcare professionals may gain insights into a patient's cardiac health, identify abnormalities, and make diagnostic or prognostic assessments.

In non-limiting examples, and still referring to FIG. 1, an ECG signal may pass through a feature model 112 layers, feature maps are generated, which capture spatial and temporal patterns in the data. These features may then be flattened into a one-dimensional or multidimensional feature vector representing the learned features from the cardiovascular measurements. For instance and without limitation, feature vector may include a vector, matrix, and/or tensor of values output by a neural network and/or matrix. Outputs of the neural network may be feature vector elements (i.e. matrix cells, vector elements etc.). It should be noted that when features extracted from scan data are flattened into a one or multidimensional feature vector, it means that the individual features are organized into a structural format suitable for analysis or input into machine learning algorithms. In a nonlimiting example, in a one-dimensional feature vector, each feature extracted from the electrical measurements (i.e. scan data) is represented as a single value arranged sequentially in a linear array. In a specific nonlimiting example, if multiple features are extracted from an ECG signal (i.e. amplitude or QRS complex, duration of P wave), they are concatenated into a one-dimensional vector, forming a signal row or column of feature values. In a multi-dimensional feature vector, features are organized into a structured array or matrix format, typically with rows representing individual samples or instances and columns representing different features. Each row of the multi-dimensional vector corresponds to a specific observation or data point such as an individual ECG or EEG recording (or other scan data 108), while each column represents a different feature extracted from the electrical measurements. This format allows for the representation of multiple observations and their associated features in a compact and structured manner, facilitating analysis and modeling tasks.

With continued reference to FIG. 1, in another embodiment feature model 112 may include feature extraction from medical records (i.e. EHRs, demographic data, additional datasets 128). Feature model 112 may also receive and process medical records 128 containing textual or structured information such as patient demographics, medical history laboratory test results, medication records, and/or comorbidities. Natural language processing (NLP) techniques or embeddings may be applied to textual data to convert it to numerical representations suitable for input into feature model 112. Structured data may be directly input into feature model 112 after preprocessing such as normalization or encoding.

Still referring to FIG. 1, processor 104, may be configured to generate at least a feature vector from a plurality of scan data 108 by at least a feature model 112. Feature model 112 may be configured to generate a feature vector from a plurality of scan data 108 by gathering, by a learning feature, at least a special feature of the plurality of scan data 108. In the context of this disclosure, special features relate to scan data 108. For the purposes of this disclosure "special feature(s)" is a feature representing relevant characteristics and/or patterns from raw electrical signals. Special features may include the voltage-time data stemming from the ECG and/or image data from Echocardiograms or EEGs. It should be noted that special features may include the input layer of feature model 112. This voltage-time data features may include, but not limited to, the global maxima of the voltage spike from an ECG relating to voltage level, length of the PR interval, length of the QRS complex, length of the QT interval, deformities within the ECG data 108 etc. It should be noted that there could be many special features relating to scan data 108 and the above list should not be considered limiting. Feature model 112 may include a neural network with one or more hidden layers. The plurality of hidden layers may include special features of scan data 108. Hidden layers in this context may include the intermediate layers situated between the input and output layers. Hidden layers may not be directly observable from the input or the output of feature model 112. Feature model 112 may further output a feature vector from the at least special features described in the hidden feature.

Still referring to FIG. 1, in some embodiments of the apparatus disclosed herein, the feature vector may include a matrix having a plurality of rows and a plurality of columns; the plurality of rows may correspond to a temporal dimension and the plurality of columns may correspond to a spatial dimension. A vector will be defined below. In some such embodiments, each of the plurality of columns correspond to one of the plurality of leads from scan data and each of the plurality of columns may correspond to a timestamp. In some embodiments, the temporal dimension may have a resolution of about 500 Hz. In some embodiments, the temporal dimension may be 200-800 Hz. In some embodiments, the temporal dimension may be 300-700 Hz. In some embodiments, the temporal dimension may be 400-600 Hz. In some embodiments, the temporal dimension may be 450 to 550 Hz. In some embodiments, the convolutional neural network may include one or more convolutional blocks and one or more fully connected blocks. In a nonlimiting example of a convolutional network tailored for analyzing physiological signals (with scan data 108), may include multiple convolutional blocks followed by one or more fully connected blocks. In the convolutional blocks, the network applies convolutional layers to extract features from temporal sequences of electrical measurements or scan data. These convolutional layers employ filters to capture local patterns and spatial relationships within the signal, enabling the network to discern relevant features such as waveform morphology, frequency components, or temporal dynamics. Subsequent pooling layers may be used to downsample the feature maps and enhance the network's translational invariance. Following the convolutional blocks, fully connected blocks process the extracted features and perform classification or regression tasks based on learned representations, allowing the network to predict clinical outcomes, diagnose abnormalities, or detect patterns indicative of specific physiological states. By leveraging convolutional and fully connected layers, this network architecture may effectively analyze and interpret complex patterns in scan data and more specifically physiological activity, facilitating applications in healthcare monitoring, diagnosis and treatment.

With continued reference to FIG. 1, a "vector" as defined in this disclosure is a data structure that represents one or more a quantitative values and/or measures of scan data and EHRs or additional datastores. Such vector and/or embedding may include and/or represent an element of a vector space; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. A vector may be represented as an n-tuple of values, where n is one or more values, as described in further detail below; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent, for instance as measured using cosine similarity as computed using a dot product of two vectors; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute $l$ as derived using a Pythagorean norm: $l = \sqrt{\sum_{i=0}^{n} a_i^2}$, where ai is attribute number i of the vector. Scaling and/or normalization may function to make vector comparison independent of absolute quantities of attributes, while preserving any dependency on similarity of attributes. A two-dimensional subspace of a vector space may be defined by any two orthogonal vectors contained within the vector space. Two-dimensional subspace of a vector space may be defined by any two orthogonal and/or linearly independent vectors contained within the vector space; similarly, an n-dimensional space may be defined by n vectors that are linearly independent and/or orthogonal contained within a vector space. A vector's "norm' is a scalar value, denoted ||a|| indicating the vector's length or size, and may be defined, as a non-limiting example, according to a Euclidean norm for an n-dimensional vector a as:

$$\|a\| = \sqrt{\sum_{i=0}^{n} a_i^2}$$

Still referring to FIG. 1, feature model 112 may include at least a neural network. The neural network may include at least a deep learning network. The neural network may include a plurality of convolutional blocks and fully connected blocks. Nonlimiting embodiments of a neural network are feedforward networks, convolutional neural networks (CNN), recurrent neural networks (RNN), recursive neural networks, Echo state networks, deep recurrent networks etc. It is to be noted that a neural network and a deep learning network will be defined below in FIG. 3 description. A neural network may include a residual connection. For the purposes of this disclosure, a "residual connection" is a component in the architecture of a deep neural network which involves bypassing one or more layers in a neural network by adding the input of a layer to its output. In an embodiment, feature model 112 may comprise a deep neural network (DNN). As used in this disclosure, a "deep neural network" is defined as a neural network with two or more hidden layers. Neural network is described in further detail below with reference to FIG. 3. In a non-limiting example, feature model 112 may include a convolutional neural network (CNN). Generating a feature vector may include training CNN using a plurality of EHR examples 140 or scan data examples 136 and generating a disease indication or outputting population and disease classifications using trained CNN. A "convolutional neural network," for the purpose of this disclosure, is a neural network in which at least one hidden layer is a convolutional layer that convolves inputs to that layer with a subset of inputs known as a "kernel," along with one or more additional layers such as pooling layers, fully connected layers, and the like.

With continued reference to FIG. 1, in some cases, CNN may include, without limitation, a deep neural network (DNN) extension. Mathematical (or convolution) operations performed in the convolutional layer may include convolution of two or more functions, where the kernel may be applied to input data e.g., ECG Data through a sliding window approach. In some cases, convolution operations may enable processor 104 to detect local/global patterns, edges, textures, and any other features described herein within ECG data. Spatial or special features may be passed through one or more activation functions, such as without limitation, Rectified Linear Unit (ReLU), to introduce non-linearities into the processing step of generating a feature vector. Additionally, or alternatively, CNN may also include one or more pooling layers, wherein each pooling layer is configured to reduce the dimensionality of input data while preserving essential features within the input data. In a non-limiting example, CNN may include one or more pooling layer configured to reduce the spatial dimensions of spatial or special feature maps by applying downsampling, such as max-pooling or average pooling, to small, non-overlapping regions of one or more features.

Still referring to FIG. 1, CNN may further include one or more fully connected layers configured to combine features extracted by the convolutional and pooling layers as described above. In some cases, one or more fully connected layers may allow for higher-level pattern recognition. In a non-limiting example, one or more fully connected layers may connect every neuron (i.e., node) in its input to every neuron in its output, functioning as a traditional feedforward neural network layer. In some cases, one or more fully connected layers may be used at the end of CNN to perform high-level reasoning and produce the final output such as, without limitation, disease indication mapping to patient or patients Further, each fully connected layer may be followed by one or more dropout layers configured to prevent overfitting, and one or more normalization layers to stabilize the learning process described herein.

With continued reference to FIG. 1, in an embodiment, training feature model (i.e., CNN) may include selecting a suitable loss function to guide the training process. In a non-limiting example, a loss function that measures the difference between the predicted representation of scan data and the ground truth 3D structure e.g., scan data examples 136 may be used, such as, without limitation, mean squared error (MSE) or a custom loss function may be designed for one or more embodiments described herein. Additionally, or alternatively, optimization algorithms, such as stochastic gradient descent (SGD), may then be used to adjust the feature model's parameters to minimize such loss. In a further non-limiting embodiment, instead of directly predicting predicted representation of scan data, feature model may be trained as a regression model to predict continuous numerical values relating to a plurality of scan data. Additionally, CNN may be extended with additional deep learning techniques, such as recurrent neural networks (RNNs) or attention mechanism, to capture additional features and/or data relationships within input data. These extensions may further enhance the accuracy and robustness of the generating.

With continued reference to FIG. 1, processor 104 may be configured to generate at least a disease indication 132 in a subject using a classification model 116. For the purposes of this disclosure, "classification model" 116 is a type of machine learning model that categorizes the ECG data, EHRs 128, additional datastores 128, demographic data 128, genomic data 128 etc., into one or more sets of classes for cardiovascular diseases, conditions, and/or deficiencies. It should be noted that additional data stores may include EHRs, demographic data, genomic data among other additional germane data. Classes generated from a classification model 116 may include centering in on specific heart issues. A class may include heart inflammation and subclasses as myocarditis positive or pericarditis positive etc. Other classes can center on specific heart diseases such as coronary heart disease arrhythmia etc. It should be noted that the classes and subclasses are not limiting. For the purposes of this disclosure, "disease indication" 132 is data result which reflects cardiovascular diseases, conditions, or deficiencies. A nonlimiting embodiments of disease indication 132 data results may be file-based formats, directory-based formats, and/or database connections. classification model 116 may include a machine learning algorithm. Apparatus 100 may train a classification model 116 with a feature vector from a feature model and disease predictions from a population classifier 120 correlated to the plurality of scan data and population disease predictions. Examples of training data may include scan data examples emulating a feature vector from a feature model 112 and/or prediction examples 144 detailed from the population classifier. Population classifier 120 may include a machine learning algorithm designed to categorize individuals into different groups or classes based on various attributes, typically derived from medical records, demographic data, genomic data, or other relevant information. Furthermore, a classification model 116 may output a disease indication 132 including a level of cardiovascular disease. It is to be noted that a subject may be connected by leads to as ECG for producing a disease indication or not.

Still referring to FIG. 1, as mentioned above, feature model 112 may contain natural language processes and thus may include a large language model (LLM). A "large language model," as used herein, is a deep learning data structure that can recognize, summarize, translate, predict and/or generate text and other content based on knowledge gained from massive datasets. Large language models may be trained on large sets of data. Training sets may be drawn from diverse sets of data such as, as non-limiting examples, novels, blog posts, articles, emails, unstructured data, electronic records, and the like. In some embodiments, training sets may include a variety of subject matters, such as, as nonlimiting examples, medical report documents, electronic health records, entity documents, business documents, inventory documentation, emails, user communications, additional datasets 128, genomic data, demographic data 128, and the like. In some embodiments, training sets of an LLM may include information from one or more public or private databases. As a non-limiting example, training sets may include databases associated with an entity. In some embodiments, training sets may include portions of documents associated with the electronic records 112 correlated to examples of outputs. In an embodiment, an LLM may include one or more architectures based on capability requirements of an LLM. Exemplary architectures may include, without limitation, GPT (Generative Pretrained Transformer), BERT (Bidirectional Encoder Representations from Transformers), T5 (Text-To-Text Transfer Transformer), and the like. Architecture choice may depend on a needed capability such generative, contextual, or other specific capabilities.

With continued reference to FIG. 1, in some embodiments, an LLM may be generally trained. As used in this disclosure, a "generally trained" LLM is an LLM that is trained on a general training set comprising a variety of subject matters, data sets, and fields. In some embodiments, an LLM may be initially generally trained. Additionally, or alternatively, an LLM may be specifically trained. As used in this disclosure, a "specifically trained" LLM is an LLM that is trained on a specific training set, wherein the specific training set includes data including specific correlations for the LLM to learn. As a non-limiting example, an LLM may be generally trained on a general training set, then specifically trained on a specific training set. In an embodiment, specific training of an LLM may be performed using a supervised machine learning process. In some embodiments, generally training an LLM may be performed using an unsupervised machine learning process. As a non-limiting example, specific training set may include information from a database. As a non-limiting example, specific training set may include text related to the users such as user specific data for electronic records correlated to examples of outputs. In an embodiment, training one or more machine learning models may include setting the parameters of the one or more models (weights and biases) either randomly or using a pretrained model. Generally training one or more machine learning models on a large corpus of text data can provide a starting point for fine-tuning on a specific task. A model such as an LLM may learn by adjusting its parameters during the training process to minimize a defined loss function, which measures the difference between predicted outputs and ground truth. Once a model has been generally trained, the model may then be specifically trained to fine-tune the pretrained model on task-specific data to adapt it to the target task. Fine-tuning may involve training a model with task-specific training data, adjusting the model's weights to optimize performance for the particular task. In some cases, this may include optimizing the model's performance by fine-tuning hyperparameters such as learning rate, batch size, and regularization. Hyperparameter tuning may help in achieving the best performance and convergence during training. In an embodiment, fine-tuning a pretrained model such as an LLM may include fine-tuning the pretrained model using Low-Rank Adaptation (LoRA). As used in this disclosure, "Low-Rank Adaptation" is a training technique for large language models that modifies a subset of parameters in the model. Low-Rank Adaptation may be configured to make the training process more computationally efficient by avoiding a need to train an entire model from scratch. In an exemplary embodiment, a subset of parameters that are updated may include parameters that are associated with a specific task or domain.

With continued reference to FIG. 1, in some embodiments an LLM may include and/or be produced using Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. An LLM may include a text prediction based algorithm configured to receive an article and apply a probability distribution to the words already typed in a sentence to work out the most likely word to come next in augmented articles. For example, if some words that have already been typed are "Nice to meet", then it may be highly likely that the word "you" will come next. An LLM may output such predictions by ranking words by likelihood or a prompt parameter. For the example given above, an LLM may score "you" as the most likely, "your" as the next most likely, "his" or "her" next, and the like. An LLM may include an encoder component and a decoder component.

Still referring to FIG. 1, an LLM may include a transformer architecture. In some embodiments, encoder component of an LLM may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. "Positional encoding," for the purposes of this disclosure, refers to a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 1, an LLM and/or transformer architecture may include an attention mechanism. An "attention mechanism," as used herein, is a part of a neural architecture that enables a system to dynamically quantify the relevant features of the input data. In the case of natural language processing, input data may be a sequence of textual elements. It may be applied directly to the raw input or to its higher-level representation.

With continued reference to FIG. 1, attention mechanism may represent an improvement over a limitation of an encoder-decoder model. An encoder-decider model encodes an input sequence to one fixed length vector from which the output is decoded at each time step. This issue may be seen as a problem when decoding long sequences because it may make it difficult for the neural network to cope with long sentences, such as those that are longer than the sentences in the training corpus. Applying an attention mechanism, an LLM may predict the next word by searching for a set of positions in a source sentence where the most relevant information is concentrated. An LLM may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation.

Still referring to FIG. 1, attention mechanism may include, without limitation, generalized attention self-attention, multi-head attention, additive attention, global attention, and the like. In generalized attention, when a sequence of words or an image is fed to an LLM, it may verify each element of the input sequence and compare it against the output sequence. Each iteration may involve the mechanism's encoder capturing the input sequence and comparing it with each element of the decoder's sequence. From the comparison scores, the mechanism may then select the words or parts of the image that it needs to pay attention to. In self-attention, an LLM may pick up particular parts at different positions in the input sequence and over time compute an initial composition of the output sequence. In multi-head attention, an LLM may include a transformer model of an attention mechanism. Attention mechanisms, as described above, may provide context for any position in the input sequence. For example, if the input data is a natural language sentence, the transformer does not have to process one word at a time. In multi-head attention, computations by an LLM may be repeated over several iterations, each computation may form parallel layers known as attention heads. Each separate head may independently pass the input sequence and corresponding output sequence element through a separate head. A final attention score may be produced by combining attention scores at each head so that every nuance of the input sequence is taken into consideration. In additive attention (Bahdanau attention mechanism), an LLM may make use of attention alignment scores based on a number of factors. Alignment scores may be calculated at different points in a neural network, and/or at different stages represented by discrete neural networks. Source or input sequence words are correlated with target or output sequence words but not to an exact degree. This correlation may take into account all hidden states and the final alignment score is the summation of the matrix of alignment scores. In global attention (Luong mechanism), in situations where neural machine translations are required, an LLM may either attend to all source words or predict the target sentence, thereby attending to a smaller subset of words.

With continued reference to FIG. 1, multi-headed attention in encoder may apply a specific attention mechanism called self-attention. Self-attention allows models such as an LLM or components thereof to associate each word in the input, to other words. As a non-limiting example, an LLM may learn to associate the word "you", with "how" and "are". It's also possible that an LLM learns that words structured in this pattern are typically a question and to respond appropriately. In some embodiments, to achieve self-attention, input may be fed into three distinct fully connected neural network layers to create query, key, and value vectors. Query, key, and value vectors may be fed through a linear layer; then, the query and key vectors may be multiplied using dot product matrix multiplication in order to produce a score matrix. The score matrix may determine the amount of focus for a word should be put on other words (thus, each word may be a score that corresponds to other words in the time-step). The values in score matrix may be scaled down. As a non-limiting example, score matrix may be divided by the square root of the dimension of the query and key vectors. In some embodiments, the softmax of the scaled scores in score matrix may be taken. The output of this softmax function may be called the attention weights. Attention weights may be multiplied by your value vector to obtain an output vector. The output vector may then be fed through a final linear layer.

Still referencing FIG. 1, in order to use self-attention in a multi-headed attention computation, query, key, and value may be split into N vectors before applying self-attention. Each self-attention process may be called a "head." Each head may produce an output vector and each output vector from each head may be concatenated into a single vector. This single vector may then be fed through the final linear layer discussed above. In theory, each head can learn something different from the input, therefore giving the encoder model more representation power.

With continued reference to FIG. 1, encoder of transformer may include a residual connection. Residual connection may include adding the output from multi-headed attention to the positional input embedding. In some embodiments, the output from residual connection may go through a layer normalization. In some embodiments, the normalized residual output may be projected through a pointwise feed-forward network for further processing. The pointwise feed-forward network may include a couple of linear layers with a ReLU activation in between. The output may then be added to the input of the pointwise feed-forward network and further normalized.

Continuing to refer to FIG. 1, transformer architecture may include a decoder. Decoder may a multi-headed attention layer, a pointwise feed-forward layer, one or more residual connections, and layer normalization (particularly after each sub-layer), as discussed in more detail above. In some embodiments, decoder may include two multi-headed attention layers. In some embodiments, decoder may be autoregressive. For the purposes of this disclosure, "autoregressive" means that the decoder takes in a list of previous outputs as inputs along with encoder outputs containing attention information from the input.

With further reference to FIG. 1, in some embodiments, input to decoder may go through an embedding layer and positional encoding layer in order to obtain positional embeddings. Decoder may include a first multi-headed attention layer, wherein the first multi-headed attention layer may receive positional embeddings.

With continued reference to FIG. 1, first multi-headed attention layer may be configured to not condition to future tokens. As a non-limiting example, when computing attention scores on the word "am," decoder should not have access to the word "fine" in "I am fine," because that word is a future word that was generated after. The word "am" should only have access to itself and the words before it. In some embodiments, this may be accomplished by implementing a look-ahead mask. A look ahead mask may include a matrix of the same dimensions as the scaled attention score matrix that is filled with "0s" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when the softmax of this matrix is taken, the negative infinities will be zeroed out; this leaves zero attention scores for "future tokens."

Still referring to FIG. 1, second multi-headed attention layer may use encoder outputs as queries and keys and the outputs from the first multi-headed attention layer as values. This process matches the encoder's input to the decoder's input, allowing the decoder to decide which encoder input is relevant to put a focus on. The output from second multi-headed attention layer may be fed through a pointwise feedforward layer for further processing.

With continued reference to FIG. 1, the output of the pointwise feedforward layer may be fed through a final linear layer. This final linear layer may act as a classifier. This classifier may be as big as the number of classes that you have. For example, if you have 10,000 classes for 10,000 words, the output of that classifier will be of size 10,000. The output of this classifier may be fed into a softmax layer which may serve to produce probability scores between zero and one. The index may be taken of the highest probability score in order to determine a predicted word.

Still referring to FIG. 1, decoder may take this output and add it to the decoder inputs. Decoder may continue decoding until a token is predicted. Decoder may stop decoding once it predicts an end token.

Continuing to refer to FIG. 1, in some embodiment, decoder may be stacked N layers high, with each layer taking in inputs from the encoder and layers before it. Stacking layers may allow an LLM to learn to extract and focus on different combinations of attention from its attention heads.

With continued reference to FIG. 1, an LLM may receive an input. Input may include a string of one or more characters. Inputs may additionally include unstructured data. For example, input may include one or more words, a sentence, a paragraph, a thought, a query, and the like. A "query" for the purposes of the disclosure is a string of characters that poses a question. In some embodiments, input may be received from a user device. User device may be any computing device that is used by a user. As non-limiting examples, user device may include desktops, laptops, smartphones, tablets, and the like. In some embodiments, input may include any set of data associated with EHRs.

With continued reference to FIG. 1, an LLM may generate at least one annotation as an output. At least one annotation may be any annotation as described herein. In some embodiments, an LLM may include multiple sets of transformer architecture as described above. Output may include a textual output. A "textual output," for the purposes of this disclosure is an output comprising a string of one or more characters. Textual output may include, for example, a plurality of annotations for unstructured data. In some embodiments, textual output may include a phrase or sentence identifying the status of a user query. In some embodiments, textual output may include a sentence or plurality of sentences describing a response to a user query. As a non-limiting example, this may include restrictions, timing, advice, dangers, benefits, and the like.

Still referring to FIG. 1, once feature vectors are generated as mentioned above from both scan data 108 and additional datasets 128, they may be combined or concatenated to form a unified representation of patient's health status. This combined feature model captures both the physiological signals from scan data 108 and contextual information from medical records 128, providing a comprehensive representation of the patient's health profile. The combined feature vector can then be fed into subsequent layers of feature model or other downstream models for output of disease indication 132. Disease indication 132 may include a level of myocarditis, as disclosed throughout this disclosure.

Still referring to FIG. 1, feature model 112 may be trained on a labeled dataset where ground truth comes in (e.g. disease diagnosis, patient outcomes) are known. During training, feature model 112 learns to extract discriminative features from scan examples 136 or EHR examples 140 etc. and optimize its parameters to minimize the loss function, such as BCE or MSE and the like. Hyperparameters including learning rate, regularization strength, and architecture design, are tuned to optimize the model's performance at hand.

Still referring to FIG. 1, processor 104 may be configured to provide instantaneous feedback of cardiovascular disease or other types of diseases when receiving a plurality of scan data. For example, an instantaneous feedback system based on receiving ECG data may be designed to provide real-time insights into cardiovascular health. Utilizing advance signal processing and machine learning models such as classification model 116, this system continuously analyzes ECG signals to detect abnormalities and provide immediate feedback to users. Processor 104 may be configured to display at least a disease indication 132. Feedback may be displayed through various options, including dedicated mobile applications, wearable devices, embedded displays and/or computer interfaces. This may enable users to monitor their hearth health conveniently and to be able to take proactive measures. Dedicated mobile applications or remote clients may provide users with real-time scan data 108 visualization, trend analysis, and alerts about potential cardiac issues. Users can access this information on user equipment. For the purposes of this disclosure, "user equipment" is any device used by an end user such as a smart phone or other mobile device, laptop, or tablet equipped with a mobile broadband adapter. Nonlimiting embodiments of wearable devices may include smartwatches, fitness trackers, and portable ECG monitors equipped with a display screen can offer continuous monitoring of ECG signals and display feedback on the device. Nonlimiting examples of embedded devices may include devices in the medical settings or clinical environments. ECG feedback can be displayed on dedicated monitors or integrated into existing healthcare systems for real-time monitoring by healthcare professionals. Processor 104 may provide for full or partial integration with existing healthcare systems. This may ensure prompt intervention in case of critical cardiac events and facilitates collaborative decision-making regarding subject care.

Still referring to FIG. 1, for example, processor 104 may be communicatively connected to a user interface 136, wherein the digital ECG may be transmitted and displayed, and processor 104 may receive user input. A "user interface," (UI) 136, as used herein, is a means by which a user and a computer system interact; for example, through the use of input devices and software. A user interface 136 may include a graphical user interface 136 (GUI), command line interface (CLI), menu-driven user interface, touch user interface, voice user interface (VUI), form-based user interface, any combination thereof, and the like. A user interface 136 may include a smartphone, smart tablet, desktop, or laptop operated by the user. In an embodiment, the user interface 136 may include a graphical user interface. A "graphical user interface (GUI)," as used herein, is a graphical form of user interface 136 that allows users to interact with electronic devices. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pulldown menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access. Information contained in user interface 136 may be directly influenced using graphical control elements such as widgets. A "widget," as used herein, is a user control element that allows a user to control and change the appearance of elements in the user interface 136. In this context a widget may refer to a generic GUI element such as a check box, button, or scroll bar to an instance of that element, or to a customized collection of such elements used for a specific function or application (such as a dialog box for users to customize their computer screen appearances). User interface 136 controls may include software components that a user interacts with through direct manipulation to read or edit information displayed through user interface 136. Widgets may be used to display lists of related items, navigate the system using links, tabs, and manipulate data using check boxes, radio boxes, and the like.

Figure 2:
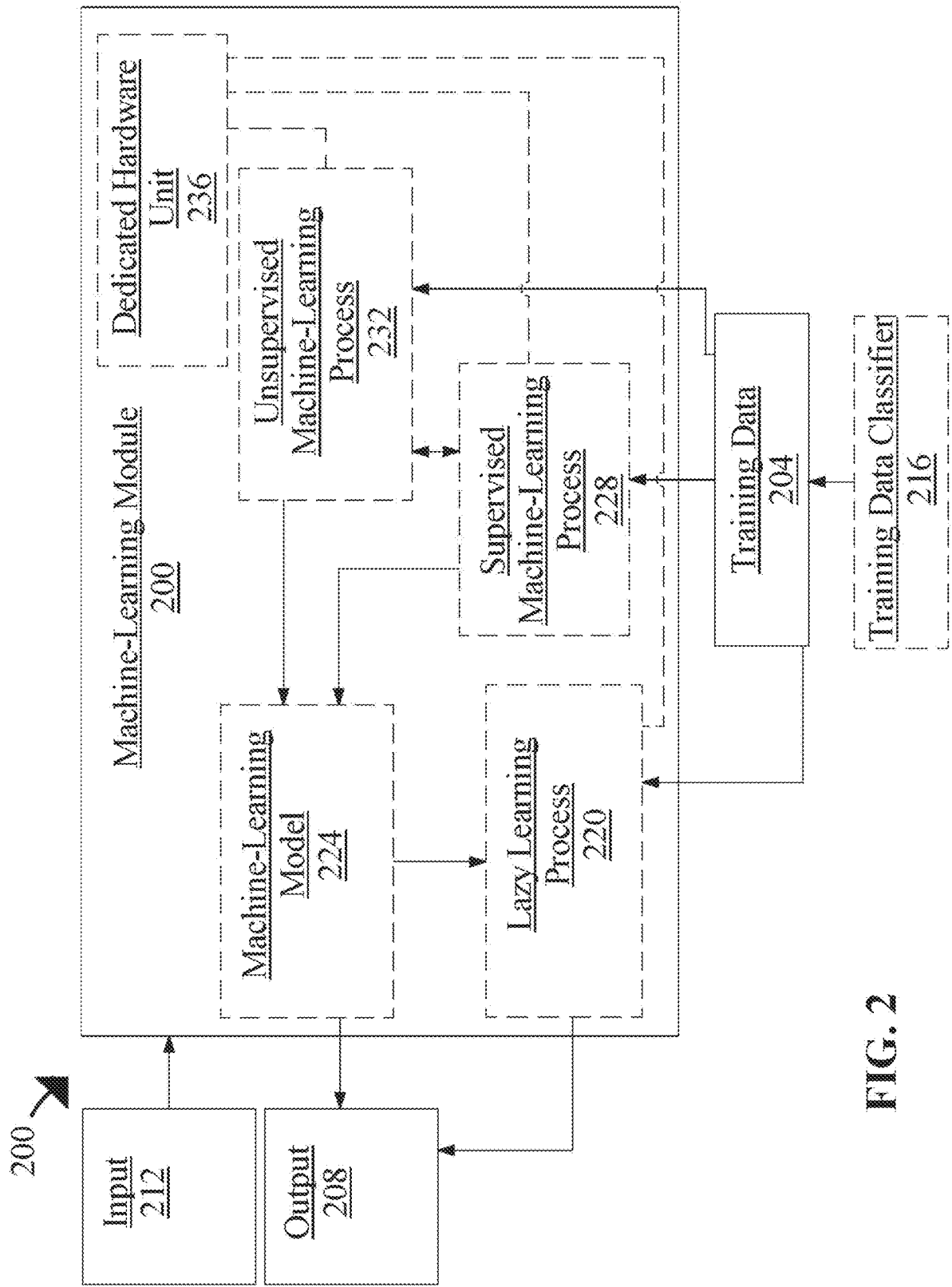
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example ECG data as primary inputs, EHRs, demographic and genomic data as ancillary inputs and a disease indication as primary outputs.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data correlates to diverse sets and subsets of the population with different diagnostic data relating to cardiac health.

Still referring to FIG. 2, computing device 204 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B) = P(B/A) P(A) \pm P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 204 may then calculate a likelihood table by calculating probabilities of different data entries and classification labels. Computing device 204 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 2, computing device 204 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 2, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l = \sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 2, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may downsample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 2, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 2, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation $\sigma$ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 2, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include a plurality of ECG data as described above as inputs, classified probabilities of disease confirmation as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods.

Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 236. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 236 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 3:
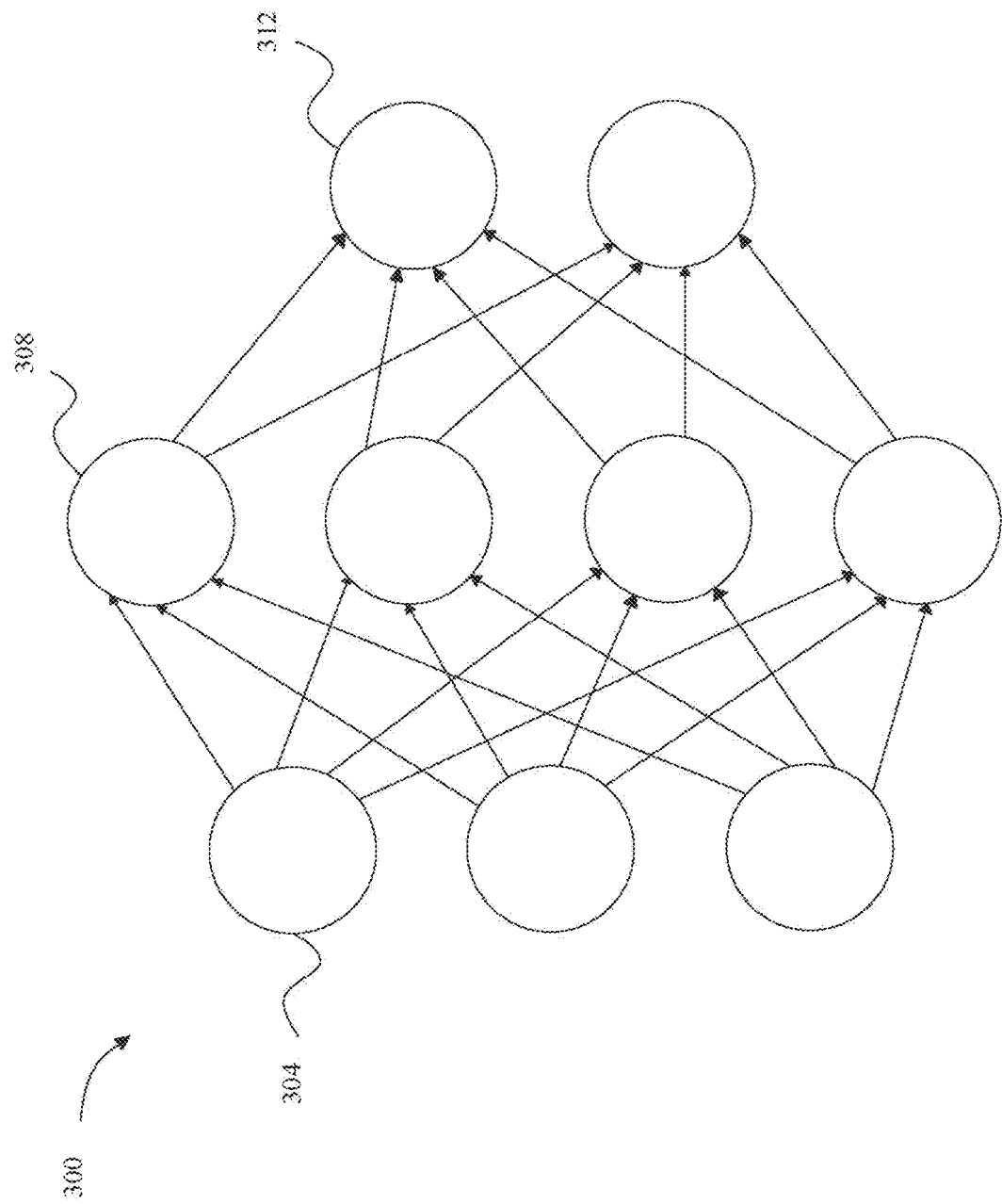
FIG. 3 is a diagram of an exemplary embodiment of a neural network.

Referring now to FIG. 3, an exemplary embodiment of neural network 300 is illustrated. A neural network 300 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 304, one or more intermediate layers 308, and an output layer of nodes 312. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 4:
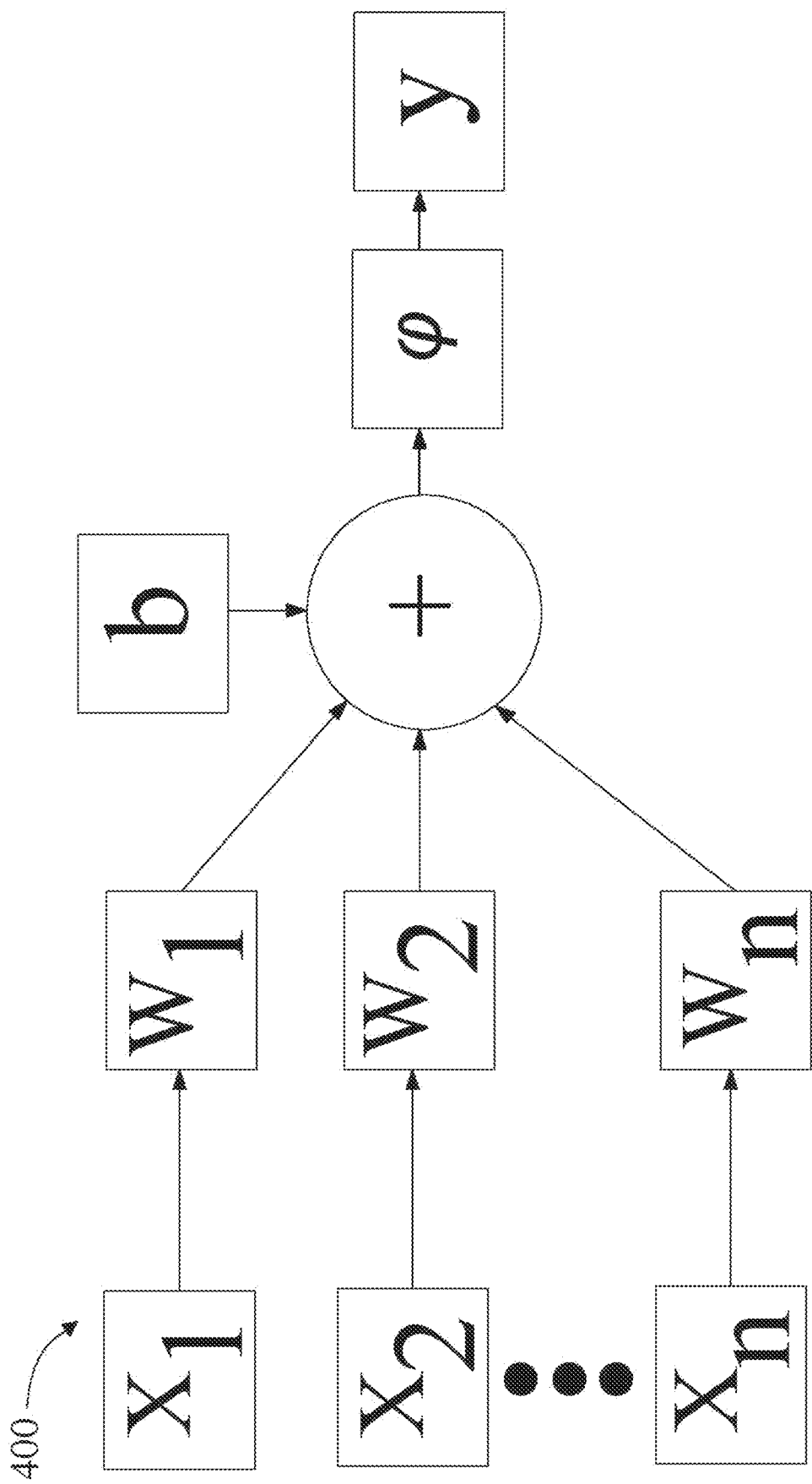
FIG. 4 is a diagram of an exemplary embodiment of a node of a neural network.

Referring now to FIG. 4, an exemplary embodiment of a node 400 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x) = \tanh^2(x)$, a rectified linear unit function such as $f(x) = \max(0, x)$, a "leaky" and/or "parametric" rectified linear unit function such as $f(x) = \max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of α (this function may be replaced and/or weighted by its own derivative in some embodiments), a softmax function such as $$f(x_i) = \frac{e^x}{\sum_i x_i}$$

herein the inputs to an instant layer are $x_i$, a swish function such as $f(x) = x*\text{sigmoid}(x)$, a Gaussian error linear unit function such as $f(x) = a(1+\tan h(\sqrt{2/\pi}(x+bx^r))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function p, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 5:
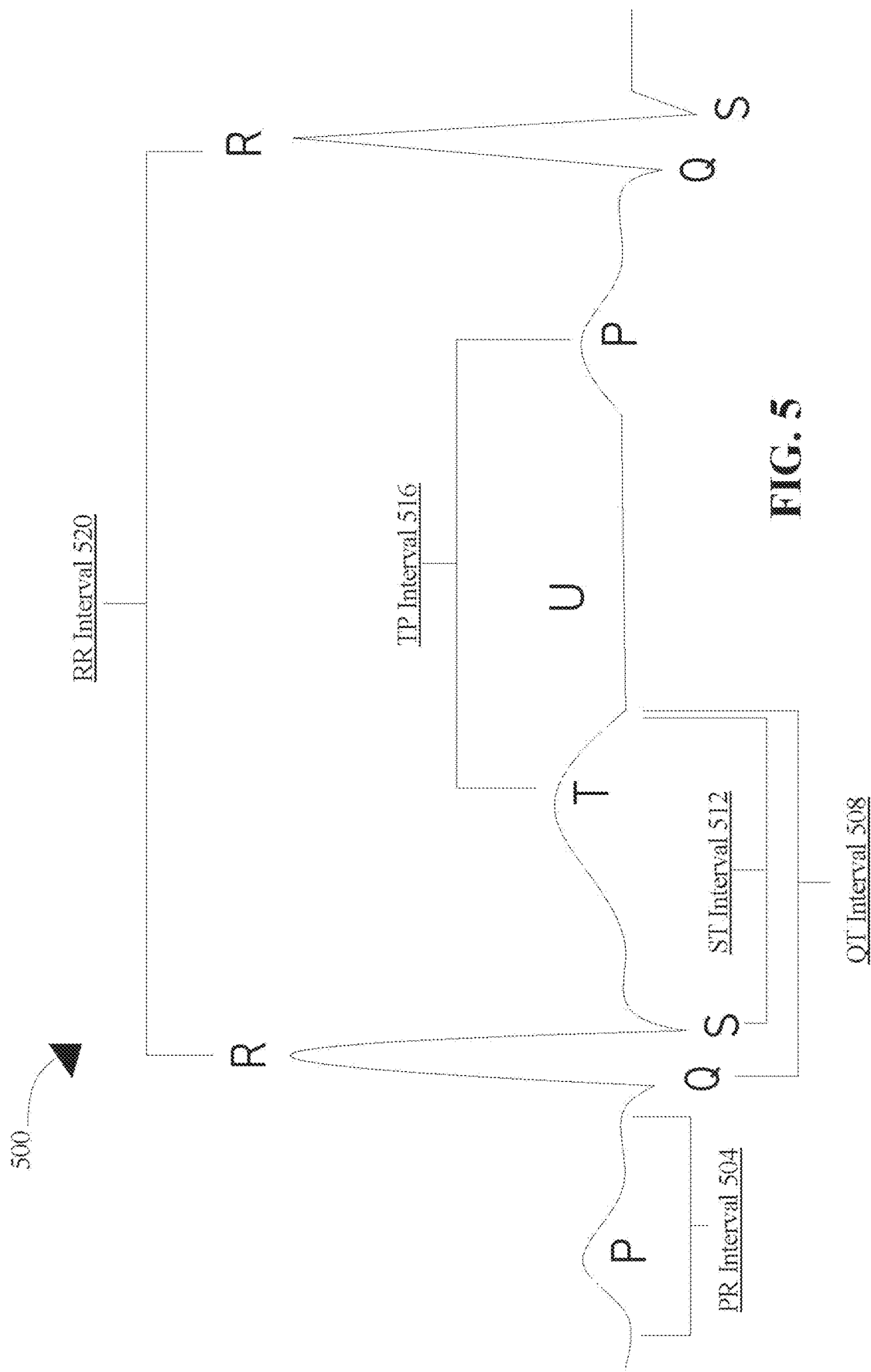
FIG. 5 is a diagram of an ECG reading.

Referring now to FIG. 5, a diagram of an ECG diagram 500 is illustrated. ECG diagram 500 may be depicted in an ECG data as described above. ECG diagram 500 may include a plurality of parameters such a PR interval 504, QT interval 508. ST interval 512, TP interval 516, RR interval 520, and the like. The P-wave may reflect atrial depolarization (activation). The PR interval 504 is the distance between the onset of the P-wave to the onset of the QRS complex. The PR interval 504 may be assessed to determine whether impulse conduction from the atria to the ventricles is normal. PR interval 504 may be measured in seconds, for example, $$\text{heart rate} = \frac{60}{PR \text{ Interval}}$$

(in seconds). The QT interval 508 may reflect the total duration of ventricular depolarization and repolarization. It may be measured from the onset of a QRS complex to the end of the T-wave. The QT duration may be inversely related to heart rate; i.e. the QT interval 508 may increase at slower heart rates and decrease at higher heart rates. Therefore, to determine whether the QT interval 508 is within normal limits, it may be necessary to adjust for the heart rate. The heart rate-adjusted QT interval 508 is referred to as the corrected QT interval 508 (QTc interval). A long QTc interval may indicate increased risk of ventricular arrhythmias. The QTc interval may be in the range of 0.36 to 0.44 seconds.

$$QT_c = \frac{QT_{interval}}{\sqrt{RR_{interval}}}$$

(measured in seconds), where RR interval 520 is the time between two consecutive R waves. The QRS complex may represent the depolarization (activation) of the ventricles which may be depicted between the Q-, R- and S-wave, although it may not always display all three waves. Since the electrical vector generated by the left ventricle is usually many times larger than the vector generated by the right ventricle, the QRS complex is a reflection of left ventricular depolarization.

Still referring to FIG. 5, the ST interval 512 is the segment on the ECG that starts at the end of the QRS complex and extends to the beginning of the T wave. It represents the early part of ventricular repolarization. The ST segment may be relatively isoelectric, meaning it is at the baseline, with minimal elevation or depression. The normal duration of the ST interval 512 is usually around 0.12 seconds (120 milliseconds). The TP interval 516 is the segment on the ECG that extends from the end of the T wave to the beginning of the next P wave. It represents the time when the ventricles are fully repolarized and are in a resting state. The duration of the TP interval 516 may be variable but is typically short, as it may represent the brief pause between cardiac cycles. Significant deviations may be associated with certain conditions affecting repolarization. The RR interval 520 is the time between two consecutive R waves on the ECG. It may represent the duration of one cardiac cycle, encompassing both atrial and ventricular depolarization and repolarization. The RR interval 520 may be measured in seconds and can be used to calculate heart rate (beats per minute) using a formula, such as $$\text{heart rate} = \frac{60}{RR \text{ Interval}}$$

(in seconds). The intervals described above may be used to determine a ventricular rate which refers to the number of ventricular contractions (heartbeats) that occur in one minute. It may be closely related to the RR interval 520 on an electrocardiogram (ECG), as the RR interval 520 represents the time between two consecutive ventricular contractions. The formula for calculating the ventricular rate (heart rate) in beats per minute (bpm) may be:

$$\text{Ventricular rate} = \frac{60}{RR \text{ Interval}}$$

(in seconds).

Myocarditis is an acquired cardiomyopathy that results from inflammation of cardiac muscle, and can be caused from a variety of etiologies including cancer, immunotherapy, auto-immune diseases, vaccinations, and infections such as COVID-19. Once myocarditis is identified, treatment involves addressing the underlying etiology when possible, and following AHA guidelines for the treatment of heart failure in those patients that develop cardiac failure.[7] Despite the value of early detection of myocarditis, there is currently no low-cost, non-invasive method for accurately screening for the disease. Currently the disease is screened for using a combination of clinical suspicion, electrocardiogram (ECG), echocardiography, the cardiac biomarker troponin, and the conducting of tests to rule out other potential causes of cardiac symptoms.[3] This approach suffers from a low specificity for detecting acute myocarditis as many cardiac insults results in ECG changes and the release of troponin from myocardiocytes[8], furthermore troponin can be insensitive for chronic myocarditis in which acute cellular death with enzyme release can lead to little or no rise in troponin.[9] Thus, in certain embodiments of the invention, contemplated herein are markers (e.g., individual markers or a panel of markers) that are underutilized, unappreciated, or not validated in the detection of acute and/or chronic myocarditis in combination with the methods disclosed herein. Such markers may include genetic/genomic markers (e.g., MicroRNA, differentially expressed genes, and gene variants), markers of myocardial injury (e.g., NT-BNP, high sensitivity Toponin I), structural proteins (e.g., VCAM-1, gelsolin, tanscin-C), and immune cells markers (e.g., LAP (+) Treg, and immune cell-associated proteins, such as heparin binding proteins and serum alarmin). Such candidate markers are disclosed in Suresh et al., Curr Heart Fail Rep. August 1: 1-10, incorporated herein by reference in its entirety. For example, and without limitation, such markers may include soluble ST2 (sST2) which is not specific to chronic forms of myocarditis and is generally a better biomarker for acute myocarditis. In certain preferred embodiments, the invention provided herein is used in conjunction with, or in addition to, standard-of-care protocols. Without being bound by any particularly theory or methodology, the invention provided herein may be used to hone a differential diagnosis and risk stratify patients (e.g., performed prior to, following, or concomitantly with a troponin lab test).

Neural networks are a form of artificial intelligence that has been widely successful in recognizing non-obvious patterns in a wide variety of health care applications including screening of mammograms 10, parsing of physician notes,[11] and detection of subtle ECG signals. It was hypothesized that all forms of myocarditis would share ECG characteristics that derived from myocardial damage and inflammation leading could be detected by a neural network. This hypothesis was tested and validated using a convolutional neural network.

Disclosed herein is the development of an artificial intelligence (AI)-based tool to detect myocarditis using paired 12-lead ECG. As provided herein, the ECG may be used with Electronic Health Record (EHR) data, including the presence of positive physician diagnosis of myocarditis in free-text notes, to train a convolutional neural network (CNN) to identify patients with myocarditis (e.g., defined as presence of positive note, a troponin lab test, a myocarditis International Classification of Diseases (ICD) code and an ECG within a fixed time window). When tested on a hold out set of 91 patients, the model disclosed herein resulted in values for AUROC, sensitivity, and specificity of 0.91, 0.83, and 0.87, respectively. Thus, the CNN model disclosed herein performs well in identifying patients with myocarditis in the derivation cohort, as well as a separate set of patients who had received vaccination against COVID-19.

All models used voltage-time information from 12-lead ECGs as inputs. Modeling techniques explored included convolutional neural networks with differing structures such as using all 12 leads as a single input.

Accordingly, in some aspects of the invention, disclosed herein are methods comprising receiving voltage-time data of a subject, the voltage-time data comprising voltage data of a plurality of leads of an electrocardiograph; generating a feature vector from the voltage-time data; providing the feature vector to a pretrained learning system; and receiving from the pretrained learning system an indication of the level of myocarditis in the subject. Generating the feature vector may comprise generating a spectrogram based on the voltage data of the plurality of leads. In some embodiments generating the feature vector comprises grouping the voltage data of the plurality of leads into a plurality of subsets.

In some embodiments, such methods further comprise receiving demographic information of the subject, wherein generating the feature vector comprises adding the demographic information to the feature vector. In some such embodiments, the method further comprises receiving genomic information of the subject. Generating the feature vector may comprise adding the genomic information to the feature vector. Without being bound by any particular methodology or theory, said genomic data may be derived from a biological sample that is derived from a patient predisposed to increased cardiovascular risk, e.g., family history or genetic and/or protein markers. In some such embodiments, the learning system comprises a convolutional neural network. Such convolutional neural networks may comprise at least one residual connection.

In some embodiments the voltage-time data of a subject is received from an electrocardiograph. In further embodiments, the voltage-time data of a subject is received from an electronic medical record.

In some embodiments, the method further comprises providing the indication to an electronic health record system for storage in a health record associated with the subject. In some embodiments, the method further comprises providing the indication to a computing node for display to a user.

In some embodiments of the methods disclosed herein, the feature vector comprises a matrix having a plurality of rows and a plurality of columns, the plurality of rows corresponding to a temporal dimension and the plurality of columns corresponding to a spatial dimension. In some such embodiments, each of the plurality of rows correspond to one of the plurality of leads and each of the plurality of columns corresponds to a timestamp. In some embodiments, the temporal dimension has a resolution of 500 Hz. The convolutional neural network disclosed herein may comprise at least nine convolutional blocks and two fully connected blocks.

Figure 6:
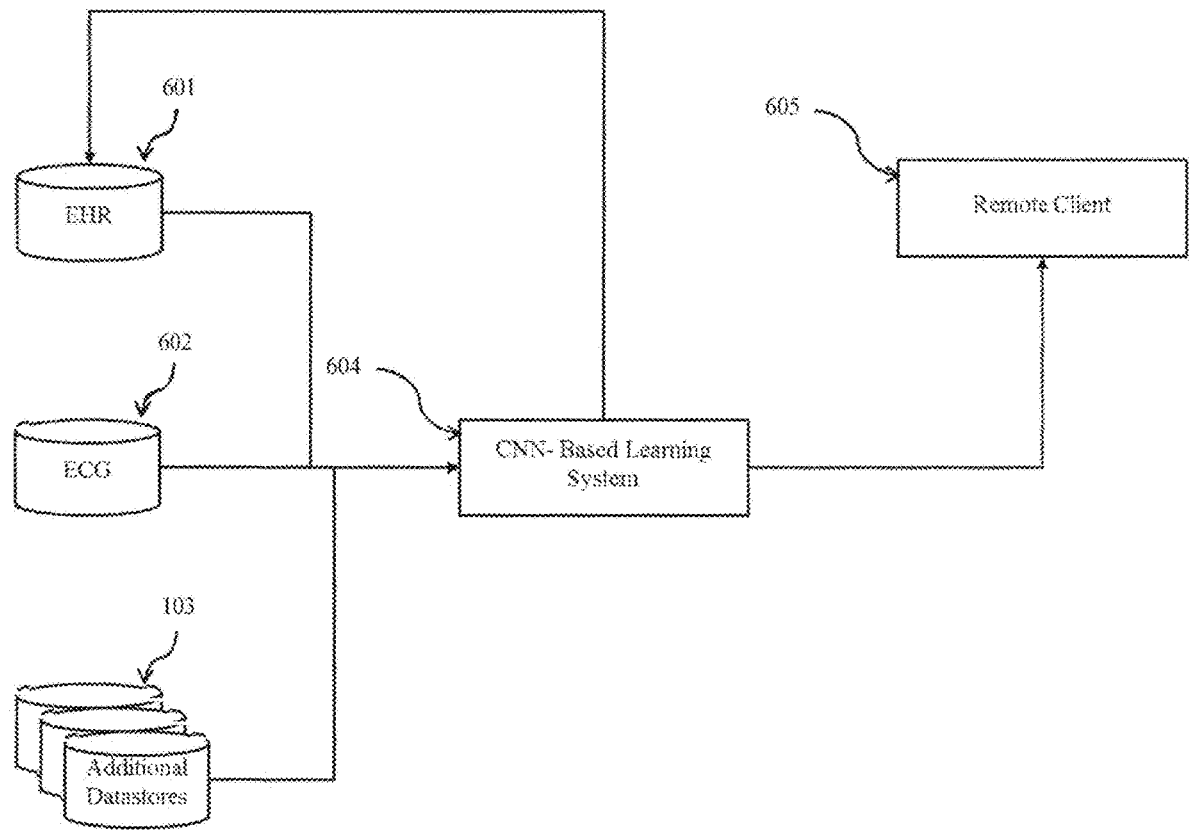
FIG. 6 is a schematic view of a system for detecting or otherwise predicting myocarditis according to embodiments of the present disclosure.

With reference now to FIG. 6, a system for detecting or otherwise predicting the level of myocarditis is illustrated according to embodiments of the present disclosure. As outlined above, in various embodiments, patient information, including electrocardiogram (ECG) data, is provided to a learning system in order to determine the level of myocarditis. Thus, aspects of the invention, as disclosed herein, also include a system comprising: an electrocardiograph comprising a plurality of leads; a computing node comprising a computer readable storage medium having program instructions embodied therewith, the program instructions executable by a processor of the computing node to cause the processor to perform a method comprising: receiving voltage-time data of a subject from the echocardiograph, the voltage-time data comprising voltage data of the plurality of leads; generating a feature vector from the voltage-time data; providing the feature vector to a pretrained learning system; and receiving from the pretrained learning system an indication of the level of myocarditis in the subject. Generating the feature vector may comprise generating a spectrogram based on the voltage data of the plurality of leads. In some embodiments generating the feature vector comprises grouping the voltage data of the plurality of leads into a plurality of subsets.

In some embodiments, such systems further comprise receiving demographic information of the subject, wherein generating the feature vector comprises adding the demographic information to the feature vector. In some such embodiments, the system further comprises receiving genomic information of the subject. Generating the feature vector may comprise adding the genomic information to the feature vector. Without being bound by any particular methodology or theory, said genomic data may be derived from a biological sample that is derived from a patient predisposed to increased cardiovascular risk, e.g., family history or genetic and/or protein markers. In some such embodiments, the learning system comprises a convolutional neural network. Such convolutional neural networks may comprise at least one residual connection.

In some embodiments the voltage-time data of a subject is received from an electrocardiograph. In further embodiments, the voltage-time data of a subject is received from an electronic medical record.

In some embodiments, the system further comprises providing the indication to an electronic health record system for storage in a health record associated with the subject. In some embodiments, the system further comprises providing the indication to a computing node for display to a user.

In some embodiments of the system disclosed herein, the feature vector comprises a matrix having a plurality of rows and a plurality of columns, the plurality of rows corresponding to a temporal dimension and the plurality of columns corresponding to a spatial dimension. In some such embodiments, each of the plurality of columns correspond to one of the plurality of leads and each of the plurality of columns corresponds to a timestamp. In some embodiments, the temporal dimension has a resolution of 500 Hz. In some embodiments, the convolutional neural network comprises at least nine convolutional blocks and two fully connected blocks.

Patient data may be received from electronic health record (EHR) 601. An electronic health record (EHR), or electronic medical record (EMR), may refer to the systematized collection of patient and population electronically-stored health information in a digital format. These records can be shared across different health care settings. Records may be shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information. EHR systems may be designed to store data and capture the state of a patient across time. In this way, the need to track down a patient's previous paper medical records is eliminated.

Electrocardiogram (ECG) data may be received directly from an electrocardiography device 602. In an exemplary 12-lead ECG, ten electrodes are placed on the patient's limbs and on the surface of the chest. The overall magnitude of the heart's electrical potential is then measured from twelve different angles (leads) and is recorded over a period of time (usually ten seconds). In this way, the overall magnitude and direction of the heart's electrical depolarization is captured at each moment throughout the cardiac cycle.

Additional datastores 603, may include further patient information as set out herein. Suitable datastores include databases, flat files, and other structures known in the art.

It will be appreciated that ECG data may be stored in an EHR for later retrieval. It will also be appreciated that ECG data may be cached, rather than delivered directly to a learning system for further processing.

Learning system 604 receives patient information from one or more of EHR 601, ECG 602, and additional datastores 603. As set out above, in some embodiments, the learning system comprises a convolutional neural network. In various embodiments, the input to the convolutional neural network comprises voltage-time information an ECG, which in some embodiments is paired with additional patient information such as demographics or genetic information.

Learning system 604 may be pretrained using suitable population data as set out in the examples in order to produce an indication of the level of myocarditis. In some embodiments, the indication is binary. In some embodiments, the indication is a probability value, indicating the likelihood of the level of myocarditis given the input patient data.

In some embodiments, learning system 604 provides the indication of the level of myocarditis for storage as part of an EHR. In this way, a computer-aided diagnosis is provided, which may be referred to by a clinician. In some embodiments, learning system 604 provides the indication of the level of myocarditis to a remote client 605. For example, a remote client may be a health app, a cloud service, or another consumer of diagnostic data. In some embodiments, the learning system 604 is integrated into an ECG machine for immediate feedback to a user during testing.

In some embodiments, a feature vector is provided to a learning system. Based on the input features, the learning system generates one or more outputs. In some embodiments, the output of the learning system is a feature vector.

In some embodiments, the learning system comprises an SVM. In other embodiments, the learning system comprises an artificial neural network. In some embodiments, the learning system is pre-trained using training data. In some embodiments training data is retrospective data. In some embodiments, the retrospective data is stored in a data store. In some embodiments, the learning system may be additionally trained through manual curation of previously generated outputs.

In some embodiments, the learning system, is a trained classifier. In some embodiments, the trained classifier is a random decision forest. However, it will be appreciated that a variety of other classifiers are suitable for use according to the present disclosure, including linear classifiers, support vector machines (SVM), or neural networks such as recurrent neural networks (RNN).

Suitable artificial neural networks include but are not limited to a feedforward neural network, a radial basis function network, a self-organizing map, learning vector quantization, a recurrent neural network, a Hopfield network, a Boltzmann machine, an echo state network, long short term memory, a bi-directional recurrent neural network, a hierarchical recurrent neural network, a stochastic neural network, a modular neural network, an associative neural network, a deep neural network, a deep belief network, a convolutional neural networks, a convolutional deep belief network, a large memory storage and retrieval neural network, a deep Boltzmann machine, a deep stacking network, a tensor deep stacking network, a spike and slab restricted Boltzmann machine, a compound hierarchical-deep model, a deep coding network, a multilayer kernel machine, or a deep Q-network.

In machine learning, a convolutional neural network (CNN) is a class of feed-forward artificial neural networks applicable to analyzing visual imagery and other natural signals. A CNN consists of an input and an output layer, as well as multiple hidden layers. The hidden layers of a CNN typically consist of convolutional layers, pooling layers, fully connected layers and normalization layers. Convolutional layers apply a convolution operation to the input, passing the result to the next layer. The convolution emulates the response of an individual neuron to stimuli. Each convolutional neuron processes data only for its receptive field.

A convolution operation, allows a reduction in free parameters as compared to a fully connected feed forward network. In particular, tiling a given kernel allows a fixed number of parameters to be learned irrespective of image size. This likewise reduces the memory footprint for a given network.

A convolutional layer's parameters consist of a set of learnable filters (or kernels), which have a small receptive field, but extend through the full depth of the input volume. During the forward pass, each filter is convolved across the width and height of the input volume, computing the dot product between the entries of the filter and the input and producing a 2-dimensional activation map of that filter. As a result, the network learns filters that activate when it detects some specific type of feature at some spatial position in the input.

In an exemplary convolution, a kernel comprises a plurality of weights $w_i \ldots w_9$. It will be appreciated that the sizes provided here are merely exemplary, and that any kernel dimension may be used as described herein. The kernel is applied to each tile of an input (e.g., an image). The result of each tile is an element of a feature map. It will be appreciated that a plurality of kernels may be applied to the same input in order to generate multiple feature maps.

Stacking the feature maps for all kernels forms a full output volume of the convolution layer. Every entry in the output volume can thus also be interpreted as an output of a neuron that looks at a small region in the input and shares parameters with neurons in the same feature map.

Convolutional neural networks may be implemented in various hardware, including hardware CNN accelerators and GPUs.

Figure 7:
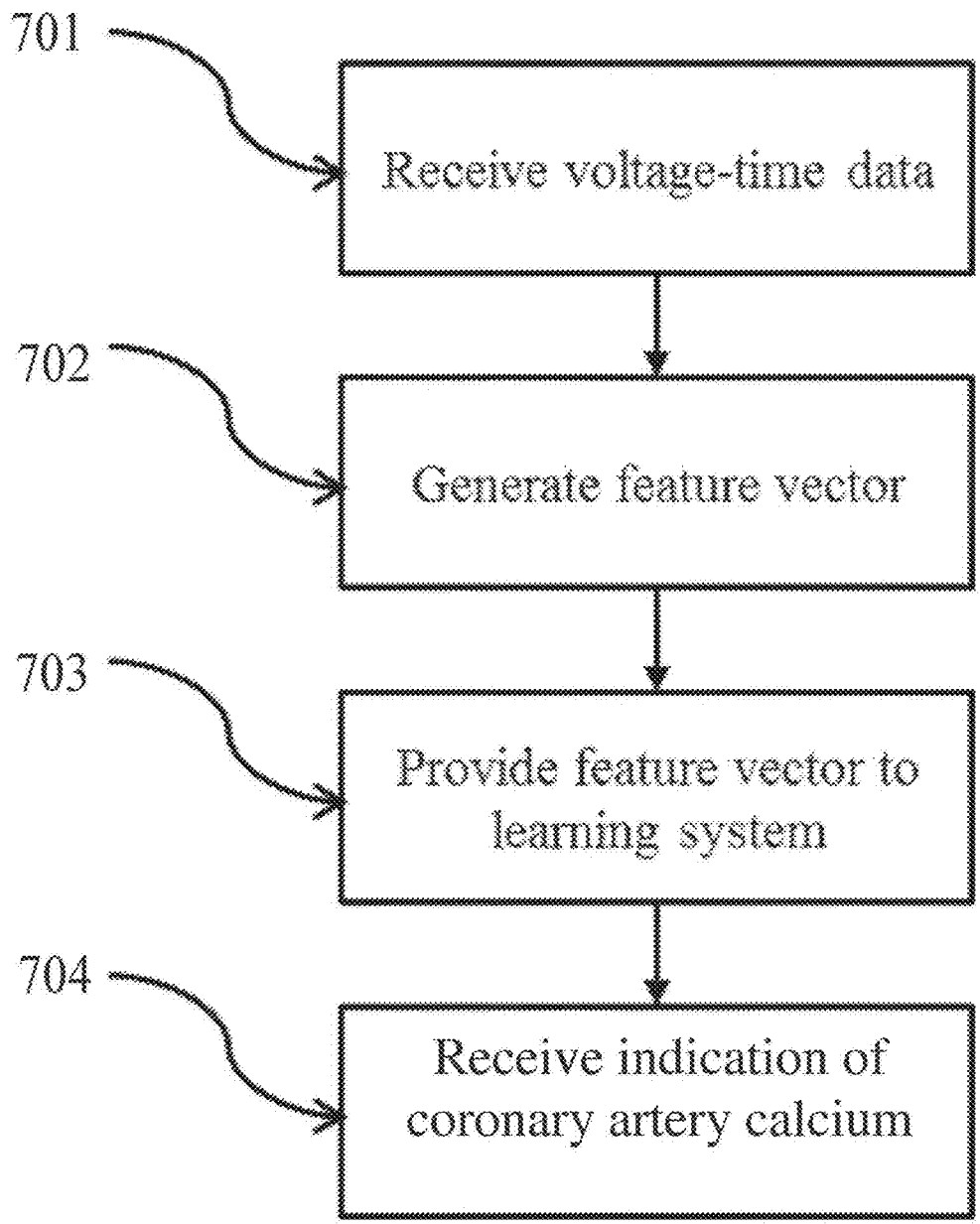
FIG. 7 a flowchart illustrating a method of detecting or otherwise predicting myocarditis according to embodiments of the present disclosure.

Referring now to FIG. 7, a flowchart is provided illustrating a method of detecting or otherwise predicting the level of myocarditis according to embodiments of the present disclosure. At 701, voltage-time data of a subject is received. The voltage-time data comprises voltage data of a plurality of leads of an electrocardiograph. At 702, a feature vector is generated from the voltage-time data. At 703, the feature vector is provided to a pretrained learning system. At 704, an indication of the presence or absence of myocarditis in the subject is received from the pretrained learning system.

Figure 8:
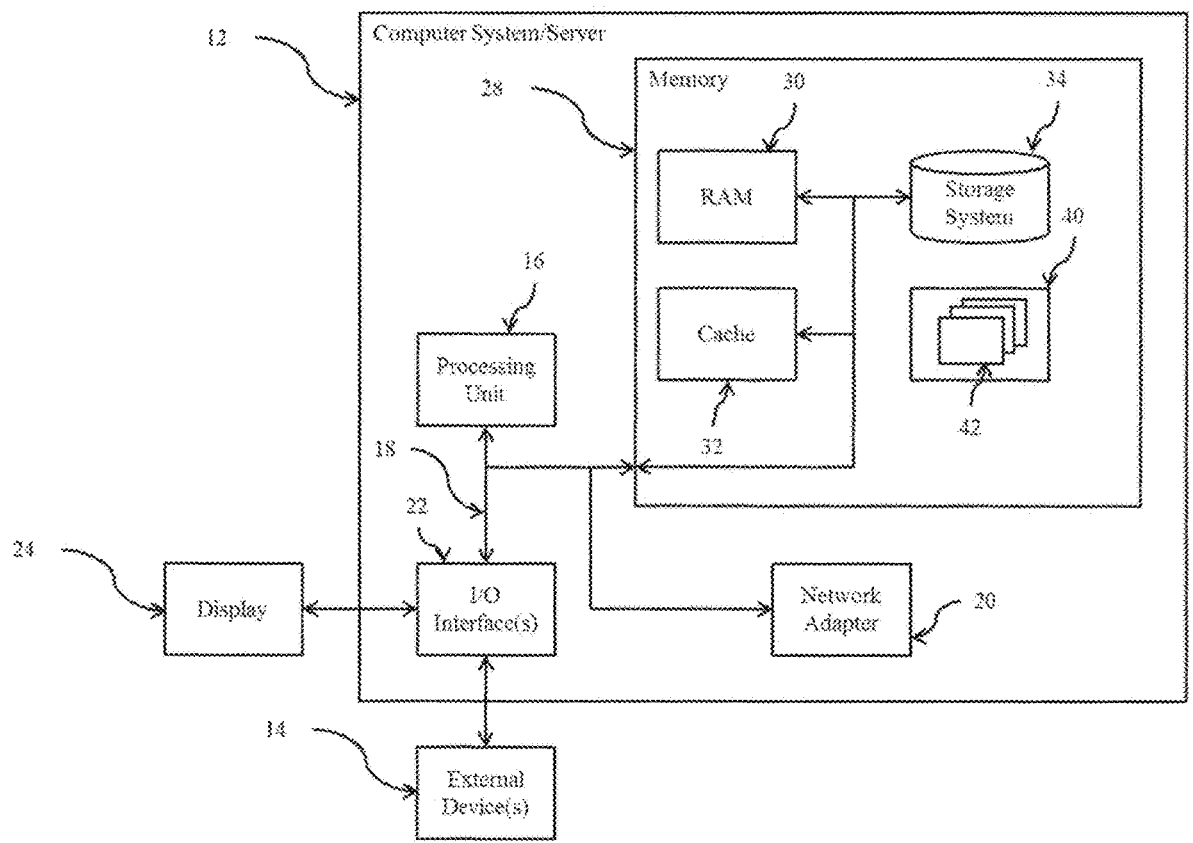
FIG. 8 depicts a computing node according to an embodiment of the present disclosure.

Referring now to FIG. 8, a schematic of an example of a computing node is shown. Computing node 10 is only one example of a suitable computing node and is not intended to suggest any limitation as to the scope of use or functionality of embodiments described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 8, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, Peripheral Component Interconnect Express (PCIe), and Advanced Microcontroller Bus Architecture (AMBA).

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present disclosure may be embodied as a system, a method, and/or a computer program product. For example, in some aspects or the invention, provided herein is a computer program product for detection and/or prediction of the level of myocarditis, the computer program product comprising a computer readable storage medium having program instructions embodied therewith, the program instructions executable by a processor to cause the processor to perform a method comprising: receiving voltage-time data of a subject from the echocardiograph, the voltage-time data comprising voltage data of the plurality of leads; generating a feature vector from the voltage-time data; providing the feature vector to a pretrained learning system; and receiving from the pretrained learning system an indication of the level of myocarditis in the subject. Generating the feature vector may comprise generating a spectrogram based on the voltage data of the plurality of leads. In some embodiments generating the feature vector comprises grouping the voltage data of the plurality of leads into a plurality of subsets.

In some embodiments, such computer program products further comprise receiving demographic information of the subject, wherein generating the feature vector comprises adding the demographic information to the feature vector. In some such embodiments, the computer program further comprises receiving genomic information of the subject. Generating the feature vector may comprise adding the genomic information to the feature vector. Without being bound by any particular methodology or theory, said genomic data may be derived from a biological sample that is derived from a patient predisposed to increased cardiovascular risk, e.g., family history or genetic and/or protein markers. In some such embodiments, the computer program product comprises a convolutional neural network. Such convolutional neural networks may comprise at least one residual connection.

In some embodiments the voltage-time data of a subject is received from an electrocardiograph. In further embodiments, the voltage-time data of a subject is received from an electronic medical record.

In some embodiments, the computer program product further comprises providing the indication to an electronic health record system for storage in a health record associated with the subject. In some embodiments, the computer program product further comprises providing the indication to a computing node for display to a user.

In some embodiments of the computer program product disclosed herein, the feature vector may comprise a matrix having a plurality of rows and a plurality of columns, the plurality of rows corresponding to a temporal dimension and the plurality of columns corresponding to a spatial dimension. In some such embodiments, each of the plurality of columns correspond to one of the plurality of leads and each of the plurality of columns corresponds to a timestamp. In some embodiments, the temporal dimension has a resolution of 500 Hz. In some embodiments, the convolutional neural network comprises at least nine convolutional blocks and two fully connected blocks.

The computer program product provided herein may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

EXAMPLES

Example 1: Methods

Data Sources and Study Population

Figure 9:
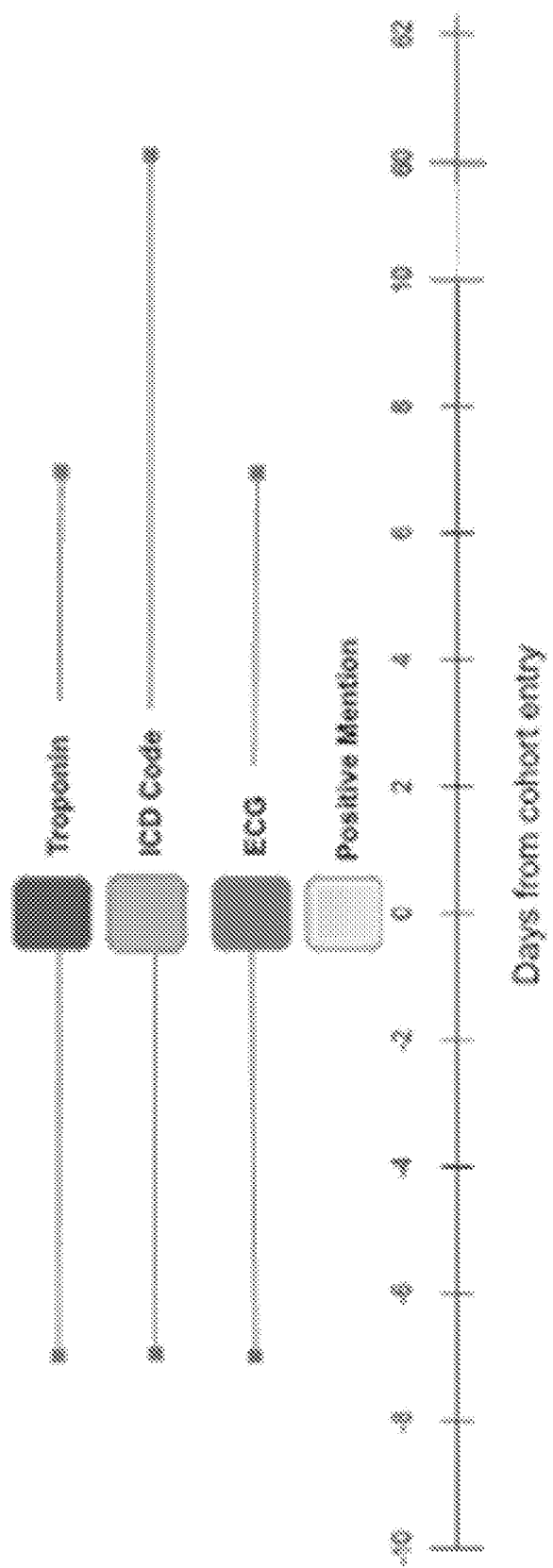
FIG. 9 depicts criterion for initial myocarditis cohort entry. Patients qualified for initial cohort entry when they had a positive mention of "myocarditis" in their clinical notes, an ECG within +/−7 days, a troponin test within +/−7 days, and an ICD-9 or ICD-10 code within −7 to +60 days of the same clinical note. All patients who made this initial cohort where then reviewed by clinical research team to assess if they qualified for entry into the final cohort.
Figure 10:
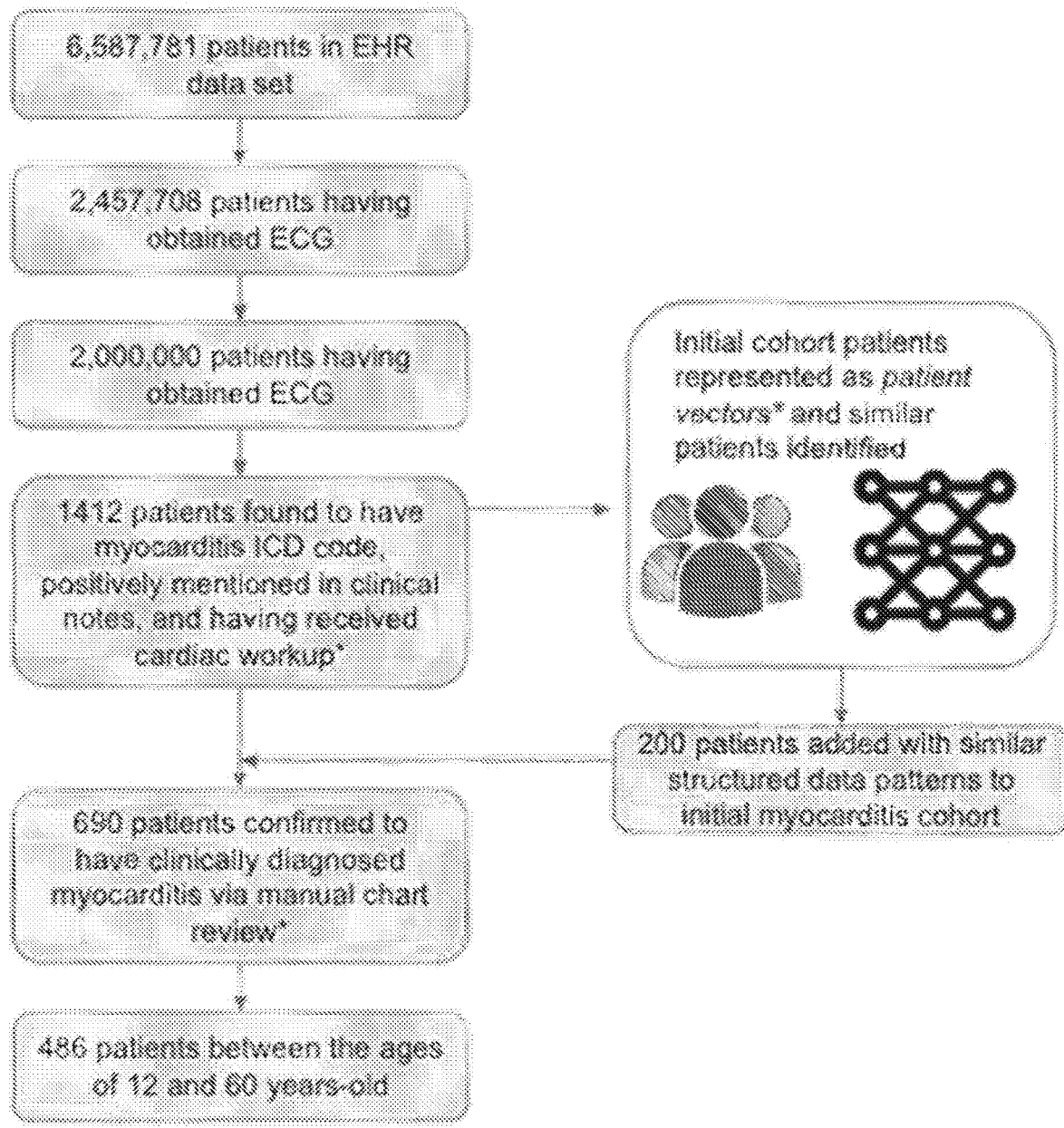
FIG. 10 depicts the myocarditis cohort creation process. Patient vectors*—each patient was represented as a vector which represented the diagnosis, procedure and medication data in the 90 days on either side of their cohort entry time. All other patients who had obtained an ECG were similarly represented in this way, and the top 200 most similar vectors were selected for manual review.

Defining Myocarditis Patients: The exemplification provided herein utilized de-identified healthcare data of 2,457,708 patients with a digital 10-lead ECG waveform with a sampling rate of 500 Hz from the Mayo Clinic Health System. The creation of this de-identified dataset was previously described[14]. From this initial data set, a subset of patients thought to have a high-likelihood of myocarditis were identified. The criteria for creating this subset is shown in FIG. 9, and included a positive mention of "myocarditis" or a synonymous term in the clinical notes using a BERT-based model previously described[11], a ICD (International Classification of Diseases) code for the disease within −7 to 60 days of the mention "myocarditis", and a troponin and an ECG within 7 days of the mention. This set of criteria was defined as an ECG and troponin and common in the workup of myocarditis. Both a free-text mention and a structured ICD-code would be expected in a true diagnosis. 1,412 patients had all of these factors, and their charts were manually reviewed. For inpatients, a patient was considered to have myocarditis if it was listed as the diagnosis or the most likely diagnosis in the notes at time of discharge. For outpatients, a patient was considered to have myocarditis if it was listed as an active problem at the time of the outpatient visit. 619 patients were found to have myocarditis as the most likely diagnosis by manual review. A further subset of 196 patients with similar patterns of ICD codes, CPT codes, a prescription within 30 days but who lacked a troponin or myocarditis ICD code were identified by a machine learning algorithm and manually reviewed. Of these cases, 71 additional myocarditis cases were identified for a total of 690 patients. From here, all cases: S12 were excluded as upon manual review myocarditis cases in this age group tended to be of substantially different etiology than in older patients. Patients age 2:60 were excluded as the rate of post-infectious and post-vaccination myocarditis is very low in elderly patients.[15] This process of initial cohort identification, cohort expansion, and manual validation is shown in FIG. 10.

Initial cohort entry was defined as occurring on the first positive mention of myocarditis in the clinical notes that satisfied all temporal constraints shown in FIG. 9. All ECGs within 1 week of cohort entry were considered to be case ECGs. As the goal was to demonstrate proof of concept of a screening tool, all ECGs within 24 hours of an intensive care CPT (Current Procedural Terminology) code were excluded as patients in the ICU often have significant iatrogenic alterations to their hemodynamics. The final result of this was 1570 ECGs associated with case patients (mean 2.3 ECGs per patient).

Selecting Control Patients: 2,457,018 patients had ECG waveforms available but did not meet inclusion criteria. Of these, patients were excluded who had any mention of "myocarditis" or a synonym in their record or who had an ICD-9 or ICD-10 code associated with myocarditis, resulting in 2,418,545 patients. Each myocarditis patient was assessed for the presence of a number of ICD-defined comorbidities at any time >30 days before cohort entry. Comorbidities were selected that would predispose patients to receiving an ECG. The same assessment was then done for the 2,451,697 non-myocarditis patients. To better match patients who were equally predisposed to receiving an ECG, propensity scores were calculated for all myocarditis and non-myocarditis patients. Finally, each myocarditis patient was matched to up to 100 control patients. All matches had the exact same age, sex, and year of ECG as well as a propensity score within 0.02 of the myocarditis patient, resulting in 48,425 control patients.

Figure 15:
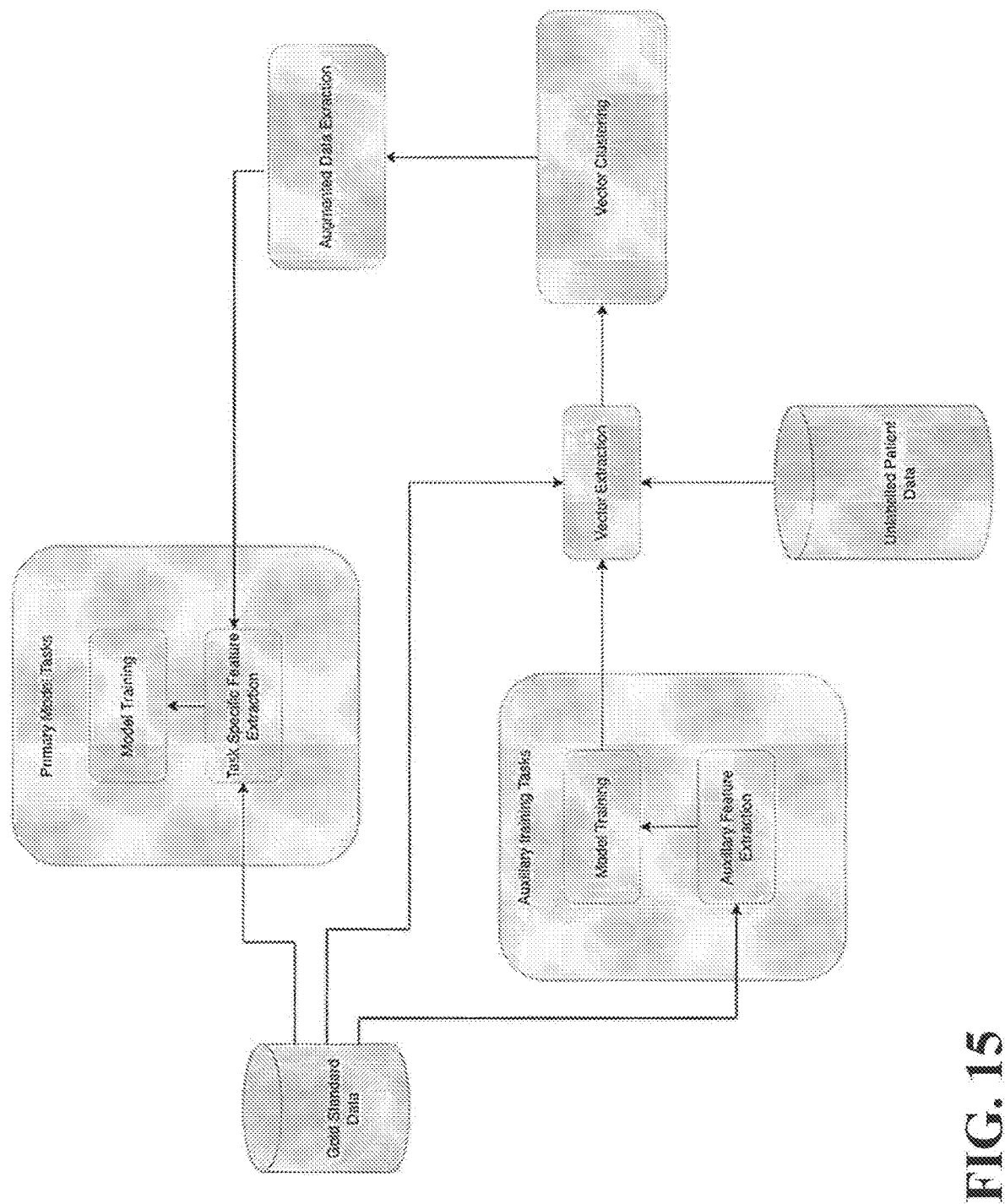
FIG. 15 depicts workflow schematic of deep-learning model including auxiliary deep neural network model to create a dense vector for every patient which represents a pattern indicating myocarditis. These vectors are then used to find patients closest to the original case or positive cohort.

Brief of Patient Embedding Clusters and Cohort Expansion: Cohort generation is a tedious, expensive process that requires domain expertise and the writing of complicated heuristics to extract high quality labeled dataset. Due to missing information, which happens quite often in HER, there exists a high possibility of missing a lot of patients in the final cohort generated. Going through all the patients with just some mention of the target disease is not practical due to the large number of mentions and the low hit rate. An ML based approach was applied to figure out potential patients based on their past medical records. A dense vector for every patient was created, which represents a pattern indicating myocarditis. Those vectors were then used to find the patients closest to the original case or positive cohort. For example, vectors were generated using the ECG model trained on the initial cohort itself. However, when using vectors generated by the primary model (i.e., the model we are trying to improve) there may be patients which have very similar features (ECG record), thus variance in the positive cohort or generalizability of the model is not improved. Thus, an auxiliary deep neural network model which uses the medical records of the patients taken in as a time series data was created to predict the onset of Myocarditis, trained using the original golden positive cohort, and then used to generate dense vectors for all the patients. These vectors were then used to find the candidate patients closest to the centroid of the golden positive cohort using cosine similarity. The auxiliary model has a deep Transformer based architecture that generates a 256 dimensional vector, which is further passed on to a linear layer (FIG. 15). The main advantage is that the original feature set is completely orthogonal to the input of the primary model so it gives a fair chance to improve the variance of the model.

Model Development

Each ECG in the myocarditis and non-myocarditis dataset was represented as a 12×5,000 matrix (12 leads x 10 second recording at 500 Hz). A convolutional neural network (CNN) was then applied using the Keras Framework with a TensorFlow backend (Google, Mountain View, California) and Python (Python Software Foundation, Beaverton, Oregon) (see Table 1 for a glossary of terms).

A training set was used to optimize the hyperparameters, batch and step size of the network. Five models were then trained (holding out 20% of ECGs each time), and these were then assembled into a final ensemble network. We tested multiple ensemble networks, and selected the one that resulted in the best AUROC (Area Under the Receiver Operating Characteristic curve).

The cohorts were split into training, testing, and validating groups representing 70%, 10%, and 20% of the dataset respectively. This resulted in 39,135 patients used for training and testing our model, and 9,776 patients for its validation. Of note, a myocarditis patient could contribute multiple ECGs to the training data set, but only 1 to the test data set. As many ECGs were available for each patient, the final ensemble model was run 50 times with random ECGs selected from a myocarditis patient in the validation set each time, and the reported AUROC is the average of those runs. Each control patient only contributed a single ECG. No patient could contribute an ECG to more than one data set (i.e., ECGs from an individual only went to train OR validation).

The model that provided the optimal AUC is similar in concept and structure to a previously developed model identifying the ejection fraction based on the 12-lead ECG (7). However, instead of single-dimensional convolutions within the leads, the current model convoluted across the leads. This resulted in a slight AUC score improvement. The model also added an additional convolution before each max pooling layer. Finally, the multiple fully connected layers at the end were replaced with a global average pooling layer, which made the model more efficient computationally and also resulted in a slight ADC-receiver-operating characteristic curve score improvement. A sigmoid function for binary classification was used as the final activation.

Example 2: Objective and Analysis

The ability of the algorithm to identify patients with a myocarditis diagnosis with only the use of a 12-lead ECG was assessed. The test set, which is a subset of the patients in Table 1, includes all types of myocarditis. After selecting the optimal neural network, the optimal threshold for detection of myocarditis was then selected. For this, a metric known as Youden's J at which the combination of sensitivity and specificity is optimized (i.e., a false positive result and false negative results are equally penalized) was used, which resulted in a threshold of 2.34%, a sensitivity of 83%, and a specificity of 86%. The model was then applied to the validation data in which an ECG was considered positive if the resulting probability value was >2.34% and performance parameters were generated. The way in which a myocarditis patient's ECG probability scores changed relative to their cohort entry time was also examined.

95% confidence intervals were estimated using Wilson score intervals. The diagnostic odds ratio and its confidence interval were used to assess the degree of discrimination for the algorithm for the subgroups analyzed.

Subgroup Analysis

Age: Using the same data and patients from the primary analysis, the patients were subdivided by age group to evaluate the sensitivity and specificity of the algorithm across different age groups.

Post-vaccination: The algorithm was additionally evaluated for its ability to detect vaccination induced myocarditis in patients who had received one of the FDA-approved vaccinations for SARS-CoV-2. There were 774,479 patients in the Mayo Clinic Health System who had received at least one dose of an FDA-approved SARS-CoV-2 vaccine. Of those patients, 574 of them had a mention of "myocarditis" or a synonymous term in a clinical note within a week of receiving their vaccination, and 192 patients had an ECG waveform during that same week. 87 of these patients lacked a diagnosis of myocarditis in their clinical notes and had no ICD codes for myocarditis and were considered to be true-negative controls. 11 of the 192 patients were found to represent true positive cases of myocarditis by clinical review of their medical records. The algorithm's sensitivity, specificity, PPV, and NPV was evaluated in this cohort.

Risk of mortality following COVID-19 Infection: The algorithm was further evaluated for its ability to identify patients with increased risk of mortality following COVID-19 infection. For this a separate set of 7,895 patients who had a positive COVID-19 PCR lab and an ECG within a window 3 days before to two weeks after their positive test were used. None of the patients had previously been seen by the algorithm. The ability of the algorithm to predict risk of mortality following COVID-19 infection was also evaluated in comparison to and in conjunction with a previously described AI algorithm for detecting patients with low left ventricular ejection fraction using a 12—lead ECG.[13]

Example 3: Results

Study Population

The sex and age distribution for the control and test sets were similar across cases and controls in the train, test, and validation sets. The myocarditis cohort had 66% male and 34% female patients, and the control cohort had 69% male patients and 31% female. Average ages of 35.8 years +/−12.7 years and 35.6+/=13.2 years were present in the case and control sets, respectively. 18,587 patients were ages 12-29 and 30,324 patients were ages 30-59. With regard to comorbidities that could predispose a patient to receive an ECG or develop myocarditis, there was no significant difference with the exception of asthma, liver disease, and lupus which were significantly higher in the myocarditis cohort than the control cohort. Patient characteristics for case and control groups in all data sets can be seen in Table 1.

TABLE 1

Patient Characteristics in Case and Control Cohorts

| | CASE | | CONTROL | |
|---|---|---|---|---|
| | Count | Percent | Count | Percent |
| Total | 486 | 100 | 48425 | 100 |
| GROUP | | | | |
| Sex | | | | |
| Male | 320 | 65.8 | 333298 | 68.8 |
| Female | 166 | 34.2 | 15127 | 31.2 |
| Age | | | | |
| 12-17 | 16 | 3.3 | 2637 | 5.4 |
| 18-24 | 107 | 22 | 10243 | 21.2 |
| 25-29 | 58 | 11.9 | 5526 | 11.4 |
| 30-39 | 117 | 24.1 | 11116 | 23 |
| 40-49 | 95 | 19.5 | 9104 | 18.8 |
| 50-59 | 93 | 19.1 | 9799 | 20.2 |
| Comorbidity | | | | |
| Cardiomyopathy | 16 | 3.29 | 1743 | 3.6 |
| CHF | 17 | 3.5 | 1407 | 2.91 |
| Myocardial Infarction | 13 | 2.67 | 1219 | 2.52 |
| Atrial Fibrillation | 8 | 1.65 | 1086 | 2.24 |
| Atrial Flutter | 4 | 0.82 | 365 | 0.75 |
| Valvular Disease | 26 | 5.35 | 2935 | 6.06 |
| Rheumatic Valvular Disease | 14 | 2.88 | 1513 | 3.12 |
| Hypertension | 62 | 12.76 | 6164 | 12.73 |
| Coronary Atherosclerosis | 14 | 2.88 | 1651 | 3.41 |
| Asthma | 25 | 5.14 | 1825 | 3.77 |
| Liver Disease | 15 | 3.09 | 1025 | 2.12 |
| Bundle Branch Block | 5 | 1.03 | 432 | 0.89 |
| Lupus | 19 | 3.91 | 773 | 1.6 |

Performance of CNN Model

Figure 11:
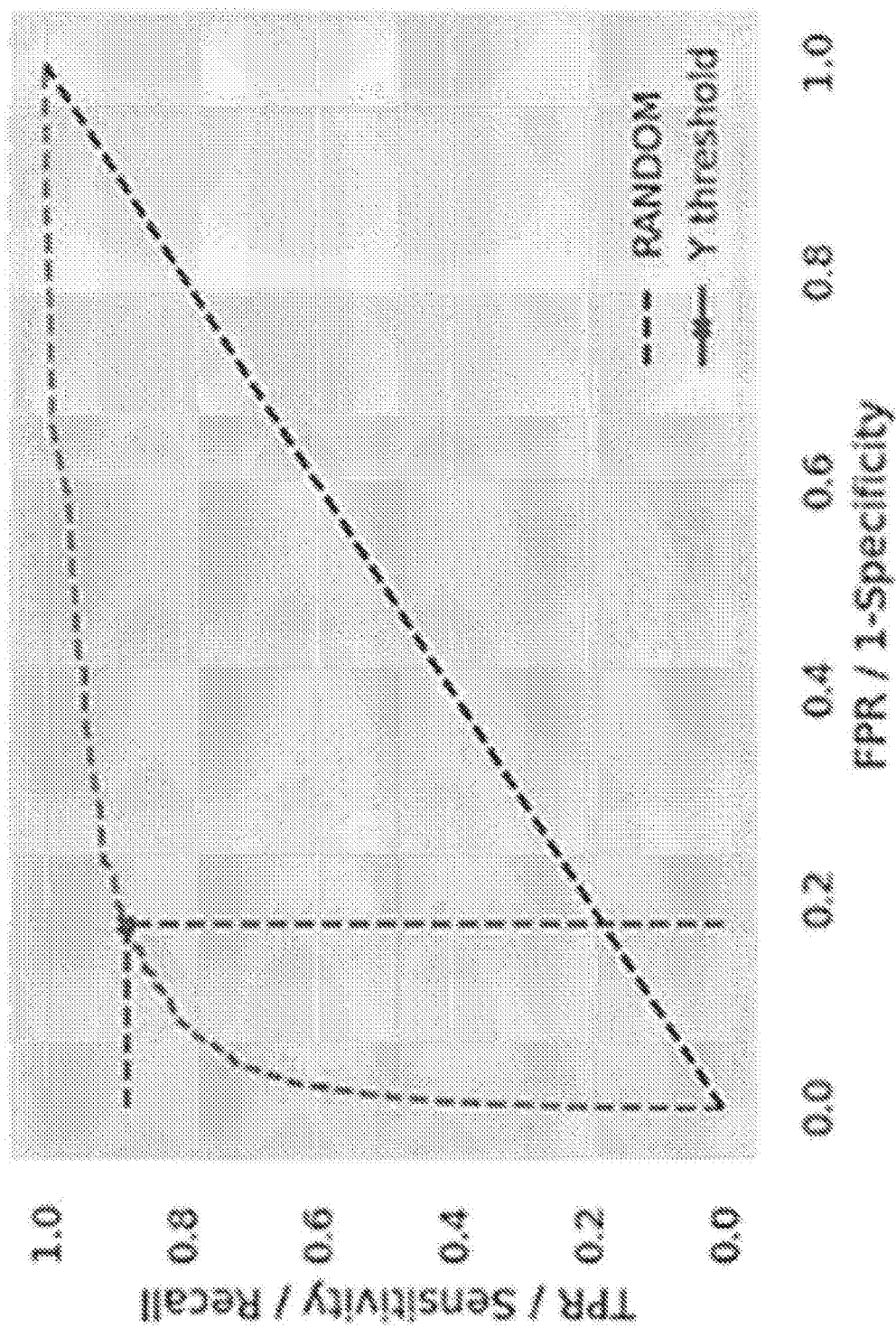
FIG. 11 depicts optimal model AUROC on the validation set. The curved dashed line represents the AUROC of the optimal model performance as tested on the validation set. The straight dashed line (m=1) is the performance that would be expect if patients were randomly labeled as having myocarditis or not. The intersecting dashed lines (x,y) indicate Youden's J, a statistic that captures the model threshold that best balances model sensitivity and specificity.

The AUROC of the CNN on the validation was 0.91 (95% CI 0.86 to 0.95) (FIG. 11). The average AUC for the 50 runs used for the final ensemble model in which a random in range ECG was selected from each myocarditis each run, the average AUC was 0.91 (95% CI 0.90 to 0.92). PPV was 5% and NPV was 99.8%.

Figure 12:
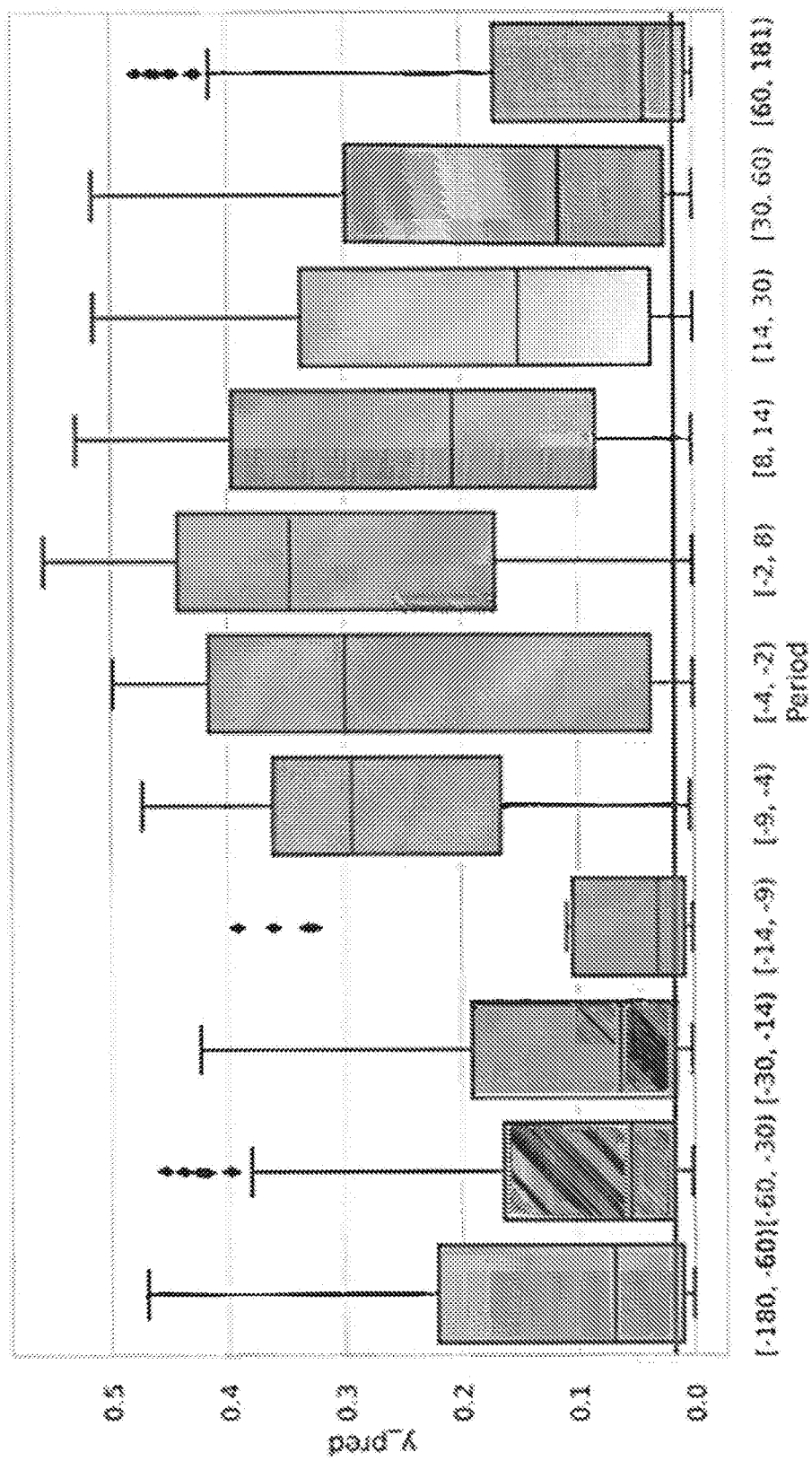
FIG. 12 depicts the model's performance on the ECGs of true positive patients before, after, and during the day of cohort entry. The greatest percentage of a true myocarditis patients ECGs were read as positive on the day of cohort entry, whereas ECGs significantly before the diagnosis of myocarditis was made and in the weeks following the diagnosis trended towards a negative. This analysis included patients with both chronic and acute myocarditis, and regardless of the amount of data present in the EHR before or after cohort entry.

FIG. 12 shows the model's performance on the ECGs of true positive patients before, after, and during the day of cohort entry. The greatest percentage of true myocarditis patients ECGs were read as positive on the day of cohort entry, whereas ECGs significantly before the diagnosis of myocarditis was made; and in the weeks following the diagnosis, trended towards a negative. This analysis included patients with both chronic and acute myocarditis, and regardless of the amount of data present in the EHR before or after cohort entry.

Subgroup Analysis

Table 2 shows the results of the model performance by age group. The model performance was moderately better in ages 12-29 than in ages 30-59, with sensitivity and specificity at the optimal threshold of 0.87 and 0.91 in the younger cohort, and 0.80 and 0.83 in older adults.

TABLE 2

MESA performance in age-stratified sub-cohorts (only test set patients)

| Age Group | True Positive | Ture Negative | False Positive | False Negative | ' Sensitivity | ' Specificity • |
|---|---|---|---|---|---|---|
| 12-17 | 5 | 492 | 33 | 0 | 100.00% | 93.71% |
| 18-24 | 14 | 1817 | 182 | 4 | 77.78% | 90.90% |
| 25-29 | 8 | 992 | 102 | 0 | 100.00% | 90.68% |
| 30-39 | 18 | 1965 | 289 | 4 | 81.82% | 87.18% |
| 40-49 | 16 | 1515 | 312 | 5 | 76.19% | 82.92% |
| 50-59 | 14 | 1582 | 404 | 3 | 82.35% | 79.66% |
| 12-29 | 27 | 3301 | 317 | 4 | 87.10% | 91.24% |
| 30-59 | 48 | 5062 | 1005 | 12 | 80.00% | 83.43% |

Application to patients who had received SARS-CoV-2 vaccination

When the algorithm was applied to the 98 patients in this cohort (11 true positive and 87 true negative) it resulted in 9 true positives, 68 true negative, 2 false negatives, and 19 false positives. This represents a PPV and NPV of 33.3% and 98% respectively. Results of this analysis are shown in Table 3.

TABLE 3

Performance metrics on MESA applied to patients who had received the COVID-19 vaccination and had a mention of "myocarditis" in their notes.

| Metric | Patient Level | ECG Level |
|---|---|---|
| True Positive | 9 | 25 |
| False Negative | 2 | 3 |
| True Negative | 68 | 91 |
| False Positive | 19 | 45 |
| Sensitivity | 0.869 ± 0.045 | 0.829 |
| Specificity | 0.776 ± 0.011 | 0.669 |
| PPV | 0.329 ± 0.015 | 0.357 |
| NPV | 0.979 ± 0.007 | 0.968 |

Predicting mortality following COVID-19 infection

Of the 7,895 patients who had an ECG in the window of time 3 days before to 2 weeks after a positive COVID-19 PCR:

- 5,675 patients were labeled negative for both low ejection fraction (EF) and myocarditis,
- 132 were screened as positive for only low EF,
- 1,696 were labeled positive for only myocarditis, and
- 392 were labeled positive for both myocarditis and low EF.

Figure 13:
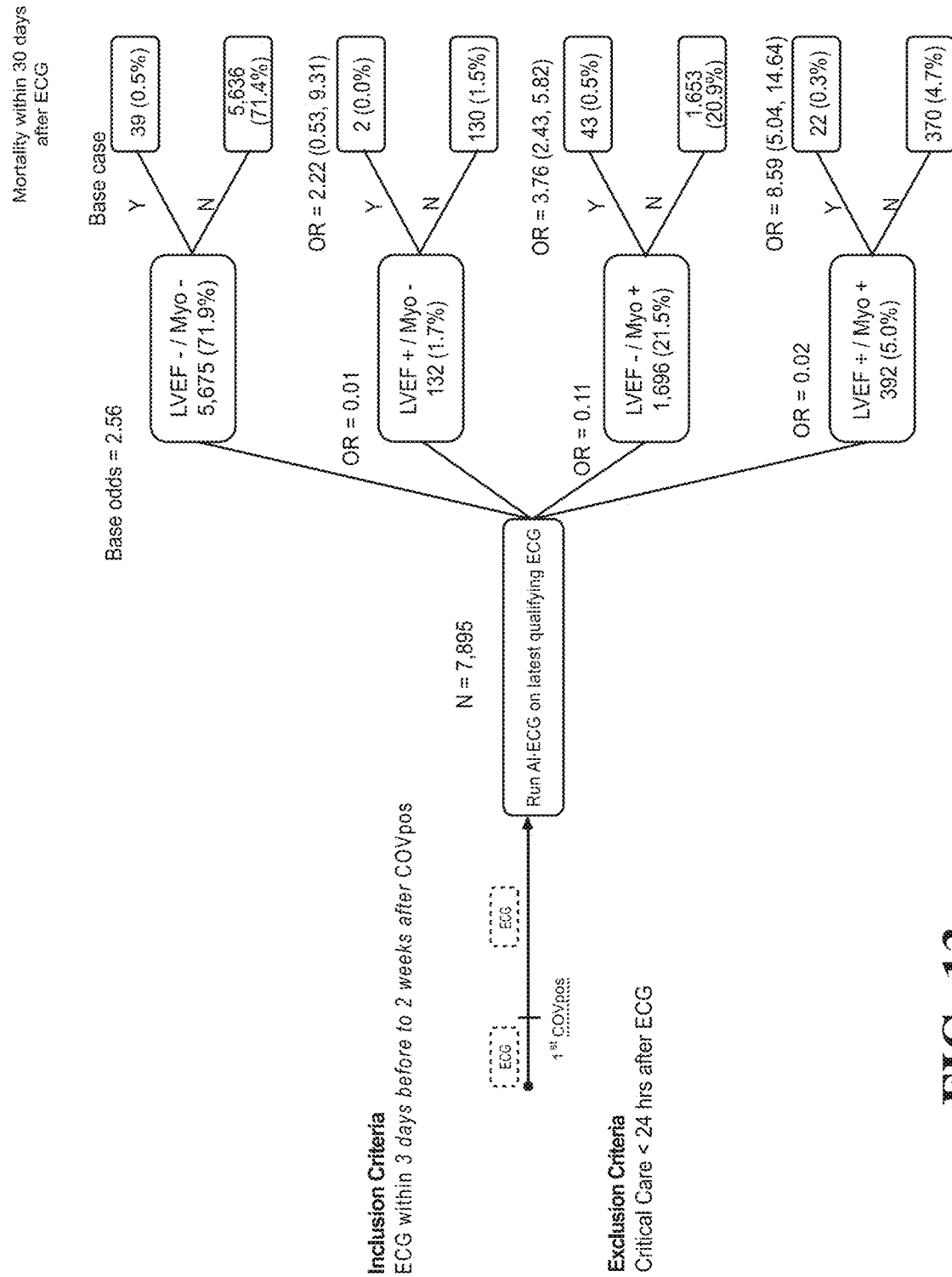
FIG. 13 depicts mortality following COVID-19 infection and ECG.

As shown in FIG. 13 an ECG that the myocarditis algorithm labeled as positive was significantly associated with a greater odds ratio for in-hospital mortality. The odds ratio was 3.76 for patients with positive myocarditis ECGs but negative for low EF ECGs, and 8.59 for patients who were considered positive by both algorithms.

Example 4: Discussion

Figure 14:
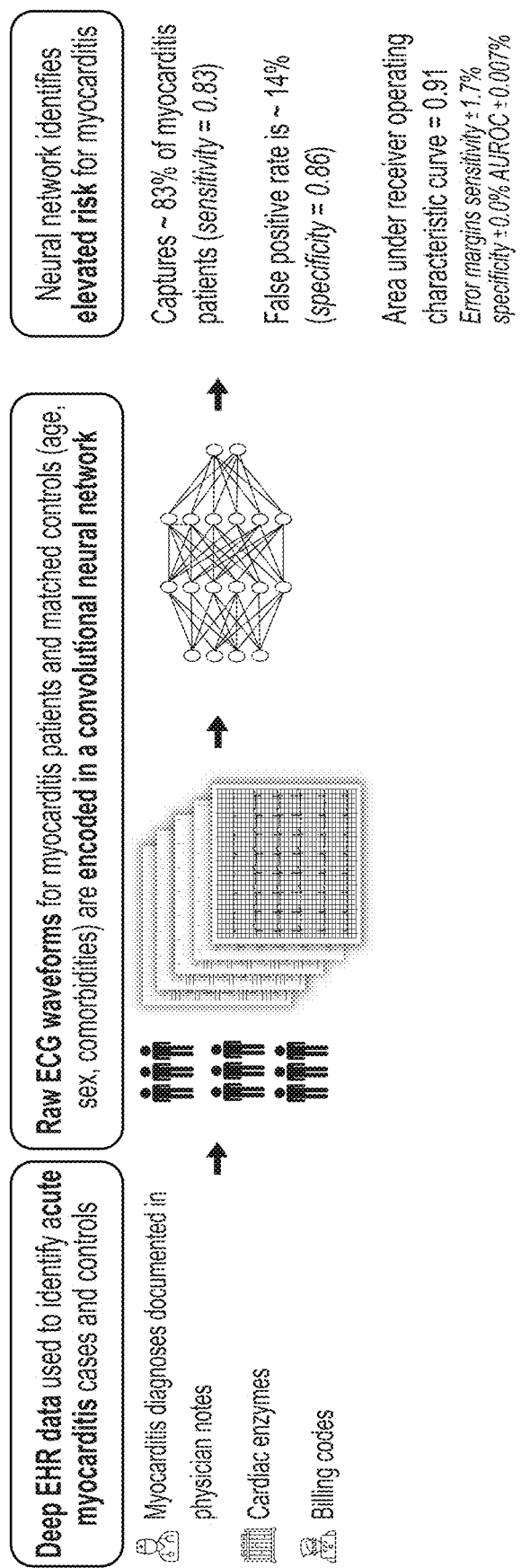
FIG. 14 depicts the study diagram of the deep-learning based methodology for detecting myocarditis using only a 12-lead ECG.

This study reports the first deep-learning based methodology for detecting myocarditis using only a 12-lead ECG (FIG. 14). The neural network shows strong ability to discriminate between patients with and without myocarditis with an AUC of 0.91. The narrow CI of 0.90 and 0.92 for the AUROC derived from 50 runs selecting different ECGs for myocarditis patients shows the model will consistently label a myocarditis patient as having the disease during a period of disease activity. The network is associated with a low false-negative rate and high negative predictive value across all cases. Of note, the model performance was best in younger patients, which is of particular note as post-vaccination and post-infectious myocarditis is a disease that particularly impacts younger individuals.15-17

Diagnosis of myocarditis is complex, as no existing diagnostic is both sensitive and specific for its diagnosis. The symptoms of myocarditis are non-specific (e.g., shortness of breath, fatigue, chest pain, palpitations) and can overlap with more common diseases such as heart failure and myocardial infarction. The gold standard diagnostic test is endomyocardial biopsy, which is invasive. Cardiac MRI can be used to identify myocarditis, but requires specialized equipment and facilities limiting accessibility to some patients, is expensive, and requires specialty training/expertise to perform and interpret. The more widely available and less invasive/expensive tests that are used in the work up of myocarditis include measurement of cardiac enzyme levels in blood and echocardiography. However, though such tests are sensitive for myocarditis, they have very poor specificity. As of yet, screening for the disease has been impractical using ECGs, as previous efforts have shown that while there are some ECG correlates for the disease, they are varied, insensitive and non-specific.18,19 The model described herein is the first application of a CNN that was agnostic to any specific ECG features in its development and can detect a wide variety of subtle changes that can be indicative of disease.

Appropriate screening of myocarditis in various subsets of patients, namely symptomatic young men with previous history of COVID-19 infection, is an active area of research 20-22 but the prevalence amongst all athletes with prior COVID-19 infection is low and the current screening method of cardiac MRI is not easily accessible, costly and time-intensive. As of this filing, there is no effective way to risk stratify patients to aid in decision making regarding further cardiac workup after, for example, COVID-19 infection. The AI-based approaches disclosed herein could play a valuable role for risk-stratifying patients, for those who may most benefit from further cardiac workup, and those who are low-risk for the development of clinically meaningful myocardial inflammation.

As disclosed herein, patients with a variety of different etiologies were included in the training set and the approach did not specifically train on those with post-COVID-19 or post-vaccination myocarditis. Further investigation across diverse cases will improve results.

Screening for low-prevalence disease is difficult due to a high false positive rate for even highly-specific algorithms. If applied to the population as a whole, the algorithm described herein would result in many false positive cases for every true myocarditis case. Generally, for many diagnostic tests, in order to have meaningful clinical utility, the prevalence of the target disease must not be so low that the positive predictive value of the test is low despite the test itself having good performance characteristics (sensitivity and specificity). Thus, for the algorithm disclosed herein, a reasonable "at risk" population would be patients that have a known risk factor for myocarditis (taking a particular medication or have an autoimmune condition that causes myocarditis) and are presenting with symptoms that could be consistent with myocarditis (shortness of breath, chest pain, fatigue, palpitations). For example, and without limitation, the prevalence of myocarditis in such a population may be in the 1-10% range. However, if applied to appropriately selected patients in which the prevalence of myocarditis is increased, such as those who have been infected with COVID-19 or had a vaccination against the virus and for whom myocarditis is on the differential the value of the algorithm is greatly increased as demonstrated in the analysis provided herein. In such situations, the NPV of 98% could assist in ruling out cases, and the PPV of 33% would allow for identifying positive cases without overwhelming hospitals with false positives. Likewise, if used similarly to a troponin test to hone a differential diagnosis and risk stratify patients (e.g., in addition to or supplementary to the standard of care), an AI-based screening algorithm for myocarditis would provide clinical value.

The algorithm as provided herein performed best in younger individuals. This is likely related to the fact that false-positive patients were generally much sicker than true negative cases. Younger patients generally have fewer comorbidities that may impact their ECG in subtle or not-so-subtle ways that may confound performance. Diseases such as LVF, heart failure, heart disease, liver disease, and arrhythmias are more prevalent in older adults and are known to impact ECG readings. The application of the tool for use in post-vaccination or post-COVID myocarditis would be of most value in younger patients as one study found greater than 90% of myocarditis cases occurred in patients <57 years-old.16 Furthermore, following mRNA vaccination it appears the vast majority of the increased risk is found in patients under 40, with only a modest increase in relative risk for those older than 40.15

The algorithm was able to predict patients at increased risk of in-hospital mortality. This was especially true when it was combined with a previous algorithm for detecting low EF. This result supports that the algorithm is truly detecting important cardiac pathology that can contribute to negative patient outcomes. It also highlights the potential utility of combining multiple AI algorithms to identify patients for who have a desired trait or in whom you are trying to prevent an adverse outcome.

Given that myocarditis is often a clinical diagnosis and more definitive testing is either resource intensive in the case of cardiac MRI, or highly invasive in the case of endomyocardial biopsy, an AI-diagnostic tool could help improve the diagnostic accuracy of cases that are unclear and could also reassure patients that they do not in fact have myocarditis in a time when widespread publication of the rare side-effect may be stoking vaccine hesitancy.23,34 For example, without being limited by theory or methodology, the cohort of patients that visits a clinic within 7 days of COVID vaccination and has myocarditis mentioned in the clinical notes from that visit has a 1 in 10 chance of having myocarditis. If those patients receive the ECG AI test, then the patients that receive a positive result would have a 1 in 3 chance of having myocarditis and the patients that receive a negative result would have a 1 in 50 chance of having myocarditis. Thus, costly follow-up testing can be more efficiently allocated.

While all myocarditis algorithms were validated using a variety of data sources and clinical review, it is impossible to guarantee that all patients labeled as having myocarditis truly had the disease. Most patients did not have pathology-proven disease, and the final judgment of the attending clinician in their medical notes was used to determine if a patient would be counted having myocarditis. As such it is possible that some patients had another disease. It is also possible that some patients labeled as having a "false-positive" myocarditis diagnosis in fact truly had the disease but were undiagnosed. Similarly, it is possible some of the "false-positive" patients had subclinical disease that was detected by the algorithm but at this time is not clinically relevant. This may be particularly true of patients with other forms of cardiac disease who disproportionately contributed to the algorithm's false positive rate. The racial, geographic, and socioeconomic conditions of the patients in the MCHS are not necessarily sufficiently representative of the country as a whole, and as such the algorithm may not operate as expected in other demographic groups. Finally, convolutional neural networks are often seen as a "black box" and it is difficult to explain exactly which ECG features it uses to drive its performance. This is an area of active investigation by the research team.

As provided herein, a deep-learning neural network can detect myocarditis using only a single 12-lead ECG with high diagnostic performance. With further refinement and external validation in other populations, such a model could be useful for assisting in diagnosing and risk stratifying patients for myocarditis, especially following infection with COVID-19 or mRNA vaccination.

Figure 16:
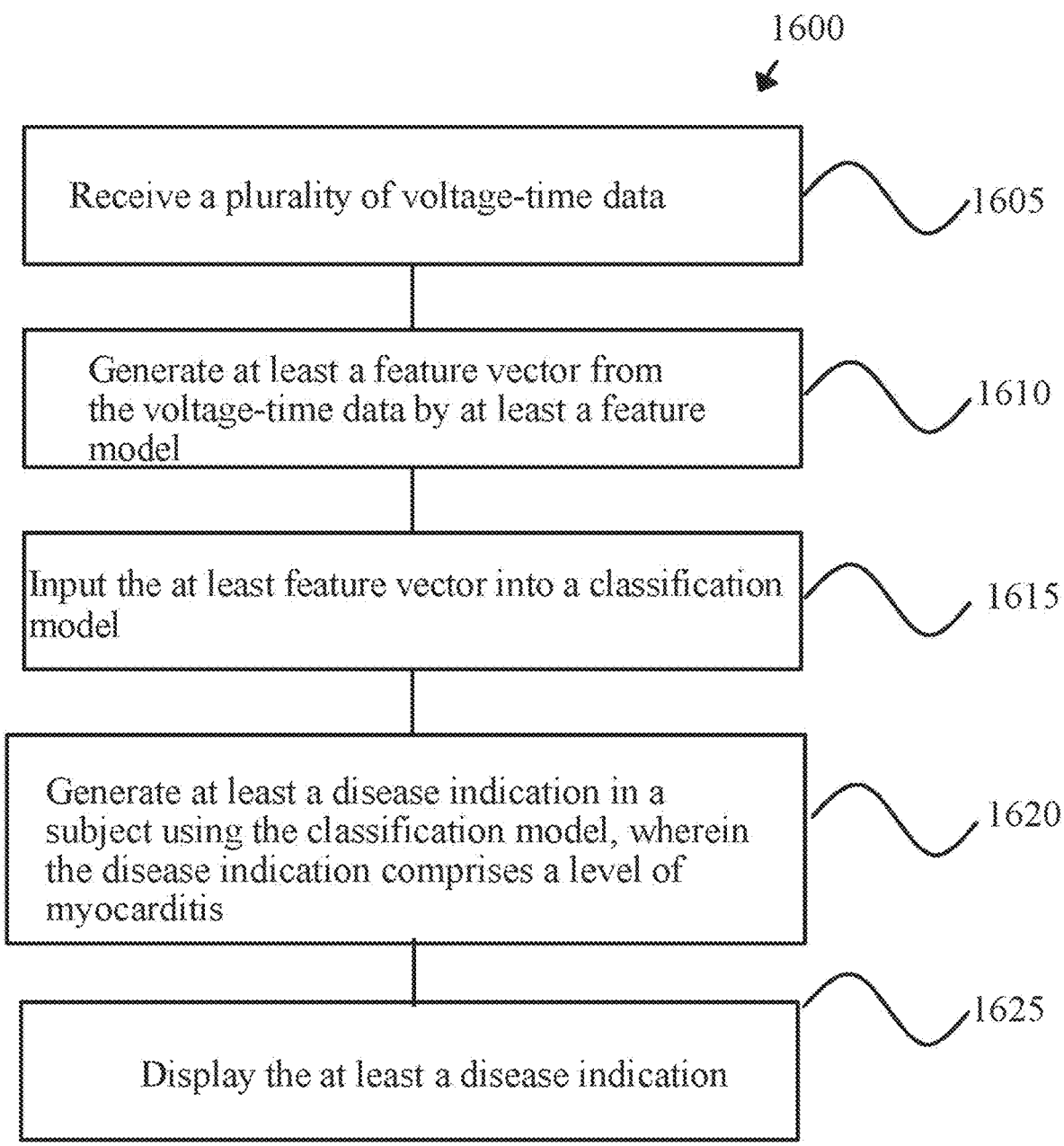
FIG. 16 is a flow diagram illustrating an exemplary work flow in one embodiment of the present invention for detecting a level of cardiovascular disease.

Referring now to FIG. 16, an exemplary diagram of a method 1600 for detecting a level of cardiovascular disease is displayed. This may be implemented as disclosed in and with reference to FIGS. 1-15. At step 1605, method 1600 includes receiving, by at least a processor, a plurality of voltage-time data. This may be implemented as disclosed in and with reference to FIGS. 1-15. At step 1610, method 1600 includes generating, by at least a processor, at least a feature vector from the voltage-time data by at least a feature model. This may be implemented as disclosed in and with reference to FIGS. 1-15. At step 1615, method 1600 includes inputting, by at least a processor, the at least feature vector into a classification model. At step 1620, method 1600 includes generating, by at least a processor, at least a disease indication in a subject using the classification model, wherein the disease indication comprises a level of myocarditis. At step 1625, method 600 includes displaying, by at least a processor, the at least a disease indication. This may be implemented as disclosed in and with reference to FIGS. 1-15.

With continued reference to FIG. 16, method 1600 may include training the feature model using a plurality of electronic health records (EHR) by training a population classifier with a plurality of EHRs and prediction data correlated to a plurality of EHR examples and prediction data examples, inputting, to the population classifier, the plurality of EHR and prediction data examples, outputting, by the population classifier, prediction of the level of cardiovascular disease in a population set, configuring the layers and activation functions of the feature model, and executing the plurality of data sets in feature model while tuning a plurality of hyperparameters. In some embodiments, training the feature model further may include preprocessing the plurality of EHRs, wherein preprocessing may include collecting the plurality of EHRs, cleaning the data within EHRs, extracting the relevant EHR features, normalizing said features, and splitting data into a plurality of data sets for training, validation and test. In some embodiments, generating the at least a feature vector from the voltage time data using the at least a feature model includes gathering, by a cardiovascular learning feature, at least a special feature of the plurality of voltage-time data, including a plurality of hidden layers, and outputting, by the learning feature, a feature vector from the at least special features described in the hidden feature. Any one of the steps above may be implemented as disclosed with reference to FIGS. 1-15.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 17:
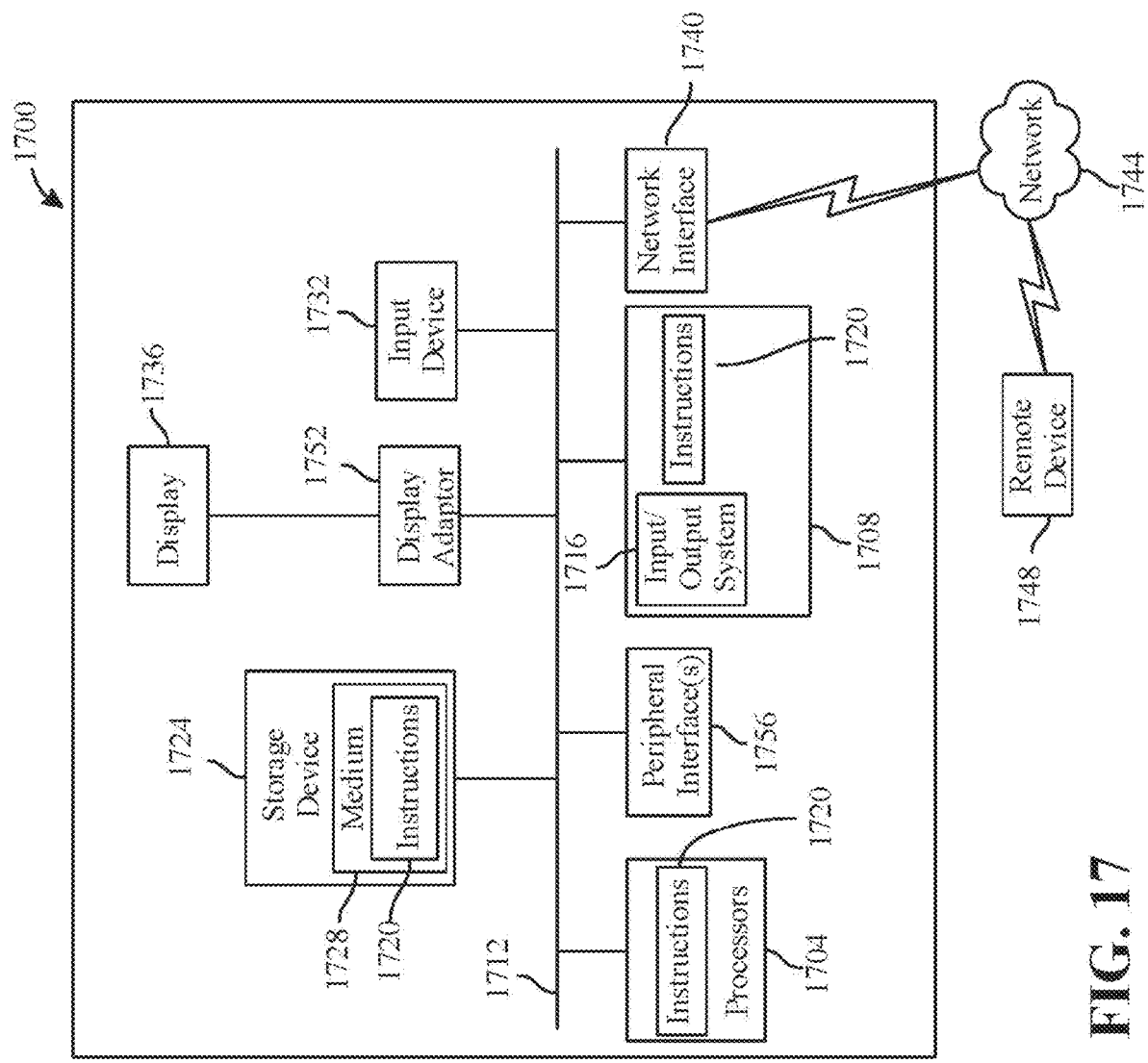
FIG. 17 is a block diagram of a computing system that can be used to implement any one or more of the methodologies disclosed herein and any one or more portions thereof.

FIG. 17 shows a diagrammatic representation of one embodiment of a computing device in the exemplary form of a computer system 1700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1700 includes a processor 1704 and a memory 1708 that communicate with each other, and with other components, via a bus 1712. Bus 1712 may include any of several types of bus structures including, but not limited to, a memory bus, a memory controller, a peripheral bus, a local bus, and any combinations thereof, using any of a variety of bus architectures.

Processor 1704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1704 may be organized according to Von Neumann and/or Harvard architecture as a non-limiting example. Processor 1704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 1708 may include various components (e.g., machine-readable media) including, but not limited to, a random-access memory component, a read only component, and any combinations thereof. In one example, a basic input/output system 1716 (BIOS), including basic routines that help to transfer information between elements within computer system 1700, such as during start-up, may be stored in memory 1708. Memory 1708 may also include (e.g., stored on one or more machine-readable media) instructions (e.g., software) 1720 embodying any one or more of the aspects and/or methodologies of the present disclosure. In another example, memory 1708 may further include any number of program modules including, but not limited to, an operating system, one or more application programs, other program modules, program data, and any combinations thereof.

Computer system 1700 may also include a storage device 1724. Examples of a storage device (e.g., storage device 1724) include, but are not limited to, a hard disk drive, a magnetic disk drive, an optical disc drive in combination with an optical medium, a solid-state memory device, and any combinations thereof. Storage device 1724 may be connected to bus 1712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1724 (or one or more components thereof) may be removably interfaced with computer system 1700 (e.g., via an external port connector (not shown)). Particularly, storage device 1724 and an associated machine-readable medium 1728 may provide nonvolatile and/or volatile storage of machine-readable instructions, data structures, program modules, and/or other data for computer system 1700. In one example, software 1720 may reside, completely or partially, within machine-readable medium 1728. In another example, software 1720 may reside, completely or partially, within processor 1704.

Computer system 1700 may also include an input device 1732. In one example, a user of computer system 1700 may enter commands and/or other information into computer system 1700 via input device 1732. Examples of an input device 1732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1732 may be interfaced to bus 1712 via any of a variety of interfaces (not shown) including, but not limited to, a serial interface, a parallel interface, a game port, a USB interface, a FIREWIRE interface, a direct interface to bus 1712, and any combinations thereof. Input device 1732 may include a touch screen interface that may be a part of or separate from display 1736, discussed further below. Input device 1732 may be utilized as a user selection device for selecting one or more graphical representations in a graphical interface as described above.

A user may also input commands and/or other information to computer system 1700 via storage device 1724 (e.g., a removable disk drive, a flash drive, etc.) and/or network interface device 1740. A network interface device, such as network interface device 1740, may be utilized for connecting computer system 1700 to one or more of a variety of networks, such as network 1744, and one or more remote devices 1748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1744, may employ a wired and/or a wireless mode of communication. In general, any network topology may be used. Information (e.g., data, software 1720, etc.) may be communicated to and/or from computer system 1700 via network interface device 1740.

Computer system 1700 may further include a video display adapter 1752 for communicating a displayable image to a display device, such as display device 1736. Examples of a display device include, but are not limited to, a liquid crystal display (LCD), a cathode ray tube (CRT), a plasma display, a light emitting diode (LED) display, and any combinations thereof. Display adapter 1752 and display device 1736 may be utilized in combination with processor 1704 to provide graphical representations of aspects of the present disclosure. In addition to a display device, computer system 1700 may include one or more other peripheral output devices including, but not limited to, an audio speaker, a printer, and any combinations thereof. Such peripheral output devices may be connected to bus 1712 via a peripheral interface 1756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for detecting a level of cardiovascular disease, the apparatus comprising:
    a 12-lead electrocardiograph comprising a plurality of leads;
    at least a processor; and
    a memory communicatively connected to the at least a processor, wherein the memory contains instructions configuring the at least a processor to:
        receive a plurality of voltage-time data of the subject from the 12-lead electrocardiograph;
        generate at least a feature vector from the plurality of voltage-time data using at least a feature model;
        input the at least feature vector into a classification model, wherein training the classification model comprises:
            receiving a plurality of 12-lead electrocardiogram signals associated with a plurality of patients;
            creating a dense vector for each subject of the plurality of subjects as a function of the plurality of 12-lead electrocardiogram signals; and applying, using a convolutional neural network (CNN), a multi-dimensional convolution operation to the plurality of 12-lead electrocardiogram across all leads of the plurality of 12-lead electrocardiogram signals at once;

generate at least a disease indication in a subject using the classification model, wherein the disease indication comprises a level of myocarditis; and display the at least a disease indication.

2. The apparatus of claim 1, wherein the apparatus is further configured to train the feature model using a plurality of electronic health records (EHR) by:

training a population classifier with a plurality of EHRs and prediction data correlated to a plurality of EHR examples and prediction data examples;

inputting, to the population classifier, the plurality of EHR and prediction data examples;

outputting, by the population classifier, prediction of the level of cardiovascular disease in a population set;

configuring layers and activation functions of the feature model; and executing the plurality of data sets in the feature model.

3. The apparatus of claim 2, wherein training the feature model further comprises preprocessing the plurality of EHRs, wherein preprocessing comprises:

collecting the plurality of EHRs;

cleaning data within the plurality of EHRs;

extracting relevant EHR features from the plurality of EHRs;

normalizing the relevant EHR features; and splitting the relevant EHR features into a plurality of data sets for training, validation and test.

4. The apparatus of claim 1, wherein the feature model comprises at least a neural network.

5. The apparatus of claim 4, wherein the neural network comprises at least a deep learning network.

6. The apparatus of claim 5, wherein the neural network comprises a plurality of convolutional blocks and a plurality of fully connected blocks.

7. The apparatus of claim 4, wherein the neural network comprises at least a residual connection.

8. The apparatus of claim 1, wherein generating the at least a feature vector from the voltage-time data using the at least a feature model comprises:

gathering, by a cardiovascular learning feature, at least a special feature of the plurality of voltage-time data;

including a plurality of hidden layers; and outputting, by the cardiovascular learning feature, a feature vector from the at least special features described in the hidden feature.

9. The apparatus of claim 1, wherein the voltage-time data comprises electrocardiogram (ECG) data.

10. The apparatus of claim 1, wherein the at least a feature vector comprises a matrix having a plurality of rows and a plurality of columns, the plurality of rows corresponding to a temporal dimension and the plurality of columns corresponding to a special dimension, wherein the temporal dimension is 450-550 Hz.

11. A method for detecting a level of cardiovascular disease, the method comprising:

receiving, by at least a processor, a plurality of voltage-time data from a 12-lead electrocardiograph comprising a plurality of leads;

generating, by at least a processor, at least a feature vector from the plurality of voltage-time data using at least a feature model;

inputting, by at least a processor, the at least feature vector into a classification model, wherein training the classification model comprises:

receiving a plurality of 12-lead electrocardiogram signals associated with a plurality of patients;

creating a dense vector for each subject of the plurality of subjects as a function of the plurality of 12-lead electrocardiogram signals; and applying, using a convolutional neural network (CNN), a multi-dimensional convolution operation to the plurality of 12-lead electrocardiogram across all leads of the plurality of 12-lead electrocardiogram signals at once;

generating, by at least a processor, at least a disease indication in a subject using the classification model, wherein the disease indication comprises a level of myocarditis; and displaying, by at least a processor, the at least a disease indication.

12. The method of claim 11, wherein the method further comprises training the feature model using a plurality of electronic health records (EHR) by:

training a population classifier with a plurality of EHRs and prediction data correlated to a plurality of EHR examples and prediction data examples;

inputting, to the population classifier, the plurality of EHR and prediction data examples;

outputting, by the population classifier, prediction of the level of cardiovascular disease in a population set;

configuring layers and activation functions of the feature model; and executing the plurality of data sets in the feature model.

13. The method of claim 12, wherein training the feature model further comprises preprocessing the plurality of EHRs, wherein preprocessing comprises:

collecting the plurality of EHRs;

cleaning data within the plurality of EHRs;

extracting relevant EHR features from the plurality of EHRs;

normalizing the relevant EHR features; and splitting the relevant EHR features into a plurality of data sets for training, validation and test.

14. The method of claim 11, wherein the feature model comprises at least a neural network.

15. The method of claim 14, wherein the neural network comprises at least a deep learning network.

16. The method of claim 15, wherein the neural network comprises a plurality of convolutional blocks and a plurality of fully connected blocks.

17. The method of claim 14, wherein the neural network comprises at least a residual connection.

18. The method of claim 11, wherein generating the at least a feature vector from the voltage-time data using the at least a feature model comprises:

gathering, by a cardiovascular learning feature, at least a special feature of the plurality of voltage-time data;

including a plurality of hidden layers; and outputting, by the learning feature, a feature vector from the at least special features described in the hidden feature.

19. The method of claim 11, wherein the voltage-time data comprises electrocardiogram (ECG) data.

20. The method of claim 11, wherein the at least a feature vector comprises a matrix having a plurality of rows and a plurality of columns, the plurality of rows corresponding to a temporal dimension and the plurality of columns corresponding to a special dimension, wherein the temporal dimension is 450-550 Hz.

\* \* \* \* \*